(12) United States Patent
Laubenthal et al.

(10) Patent No.: US 11,759,271 B2
(45) Date of Patent: Sep. 19, 2023

(54) SYSTEM AND METHOD FOR INDICATING MAPPING OF CONSOLE-BASED SURGICAL SYSTEMS

(71) Applicant: Stryker Corporation, Kalamazoo, MI (US)

(72) Inventors: Michael Laubenthal, Mattawan, MI (US); Steven T. Clifford, Byron Center, MI (US); Brett R. Merkel, Portage, MI (US); Zachary Kemp, Naples, FL (US)

(73) Assignee: Stryker Corporation, Kalamazoo, MI (US)

( * ) Notice: Subject to any disclaimer, the term of this patent is extended or adjusted under 35 U.S.C. 154(b) by 274 days.

(21) Appl. No.: 17/350,782

(22) Filed: Jun. 17, 2021

(65) Prior Publication Data

US 2021/0307847 A1    Oct. 7, 2021

Related U.S. Application Data

(63) Continuation of application No. 16/220,542, filed on Dec. 14, 2018, now abandoned, which is a
(Continued)

(51) Int. Cl.
*A61B 90/92* (2016.01)
*A61B 34/30* (2016.01)
(Continued)

(52) U.S. Cl.
CPC .............. *A61B 34/30* (2016.02); *A61B 17/00* (2013.01); *A61B 90/08* (2016.02); *A61B 90/361* (2016.02);
(Continued)

(58) Field of Classification Search
CPC ............ A61B 90/92; A61B 2090/0804; A61B 2017/00199; A61B 17/00225; A61B 2017/00973
See application file for complete search history.

(56) References Cited

U.S. PATENT DOCUMENTS

| 3,409,751 A | 11/1968 | Krieger |
| 3,439,680 A | 4/1969 | Thomas, Jr. |

(Continued)

FOREIGN PATENT DOCUMENTS

| BE | 891622 A | 4/1982 |
| CN | 101321606 A | 12/2008 |

(Continued)

OTHER PUBLICATIONS

English language abstract and machine-assisted English translation for BE 891622 extracted from espacenet.com database on Aug. 27, 2020, 5 pages.

(Continued)

*Primary Examiner* — Lynsey C Eiseman
(74) *Attorney, Agent, or Firm* — Howard & Howard Attorneys PLLC

(57) ABSTRACT

The console-based surgical system includes a footswitch having a footswitch connector line and an input visual indicator having a light emitter. The console-based surgical system includes a surgical console including instrument ports for coupling to and transmitting an energization signal to a surgical instrument and a footswitch port for coupling to and receiving a signal from the footswitch. Each instrument port includes an instrument visual indicator and the footswitch port includes a footswitch visual indicator. The indicators include a light emitter and a ring-shaped light guide. The surgical console includes a controller, which associates the footswitch port with an instrument port and activates the light emitter of the input visual indicator, the footswitch visual indicator, and the instrument visual indicator of the associated instrument port to emit a matching colored light. The controller receives a signal from the footswitch and generates and transmits an energization signal to the associated instrument port to actuate a function (Continued)

of the surgical instrument coupled to the associated instrument port.

19 Claims, 19 Drawing Sheets

Related U.S. Application Data continuation-in-part of application No. PCT/US2018/029914, filed on Apr. 27, 2018.

(60) Provisional application No. 62/491,668, filed on Apr. 28, 2017.

(51) Int. Cl.
*A61B 17/00* (2006.01)
*A61B 90/00* (2016.01)
*A61B 34/00* (2016.01)

(52) U.S. Cl.
CPC .............. *A61B 90/92* (2016.02); *A61B 34/76* (2016.02); *A61B 2017/00199* (2013.01); *A61B 2017/00221* (2013.01); *A61B 2017/00225* (2013.01); *A61B 2017/00973* (2013.01); *A61B 2090/0804* (2016.02); *A61B 2090/0807* (2016.02)

(56) References Cited

U.S. PATENT DOCUMENTS

| | | |
|---|---|---|
| 3,990,452 A | 11/1976 | Murry et al. |
| 4,051,855 A | 10/1977 | Schneiderman |
| 4,274,411 A | 6/1981 | Dotson, Jr. |
| 4,590,934 A | 5/1986 | Malis et al. |
| 4,705,038 A | 11/1987 | Sjostrom et al. |
| 4,768,496 A | 9/1988 | Kreizman et al. |
| 4,837,857 A | 6/1989 | Scheller et al. |
| 4,933,843 A | 6/1990 | Scheller et al. |
| 5,083,240 A | 1/1992 | Pasco |
| 5,091,656 A | 2/1992 | Gahn |
| 5,135,483 A | 8/1992 | Wagner et al. |
| 5,157,603 A | 10/1992 | Scheller et al. |
| 5,166,513 A | 11/1992 | Keenan et al. |
| 5,217,478 A | 6/1993 | Rexroth |
| 5,249,121 A | 9/1993 | Baum et al. |
| 5,269,794 A | 12/1993 | Rexroth |
| RE34,556 E | 3/1994 | Sjostrom et al. |
| 5,417,246 A | 5/1995 | Perkins et al. |
| 5,419,761 A | 5/1995 | Narayanan et al. |
| 5,436,542 A | 7/1995 | Petelin et al. |
| 5,455,766 A | 10/1995 | Scheller et al. |
| 5,484,400 A | 1/1996 | Edwards et al. |
| 5,549,139 A | 8/1996 | Perkins et al. |
| 5,554,049 A | 9/1996 | Reynolds |
| 5,555,161 A | 9/1996 | Roe et al. |
| 5,568,859 A | 10/1996 | Levy et al. |
| 5,632,759 A | 5/1997 | Rexroth |
| 5,803,238 A | 9/1998 | Roza |
| 5,857,485 A | 1/1999 | Perkins et al. |
| 5,883,615 A | 3/1999 | Fago et al. |
| 5,902,105 A | 5/1999 | Uejima et al. |
| 5,910,139 A | 6/1999 | Cochran et al. |
| 5,913,853 A | 6/1999 | Loeb et al. |
| 5,979,494 A | 11/1999 | Perkins et al. |
| 5,997,528 A | 12/1999 | Bisch et al. |
| 6,055,458 A | 4/2000 | Cochran et al. |
| 6,066,129 A | 5/2000 | Larson |
| 6,086,576 A | 7/2000 | Bisch |
| 6,086,598 A | 7/2000 | Appelbaum et al. |
| 6,106,512 A | 8/2000 | Cochran et al. |
| 6,117,126 A | 9/2000 | Appelbaum et al. |
| 6,179,614 B1 | 1/2001 | Elrod et al. |
| 6,216,034 B1 | 4/2001 | Hofmann et al. |
| 6,231,568 B1 | 5/2001 | Loeb et al. |
| 6,231,569 B1 | 5/2001 | Bek et al. |
| 6,251,113 B1 | 6/2001 | Appelbaum et al. |
| 6,258,087 B1 | 7/2001 | Edwards et al. |
| 6,273,886 B1 | 8/2001 | Edwards et al. |
| 6,277,083 B1 | 8/2001 | Eggers et al. |
| 6,285,693 B1 | 9/2001 | Sagehashi |
| 6,287,304 B1 | 9/2001 | Eggers et al. |
| 6,319,031 B1 | 11/2001 | Greenstein |
| 6,325,798 B1 | 12/2001 | Edwards et al. |
| 6,355,031 B1 | 3/2002 | Edwards et al. |
| 6,358,245 B1 | 3/2002 | Edwards et al. |
| 6,402,744 B2 | 6/2002 | Edwards et al. |
| 6,409,722 B1 | 6/2002 | Hoey et al. |
| 6,420,186 B1 | 7/2002 | Berger et al. |
| 6,423,058 B1 | 7/2002 | Edwards et al. |
| 6,440,128 B1 | 8/2002 | Edwards et al. |
| 6,464,689 B1 | 10/2002 | Qin et al. |
| 6,464,697 B1 | 10/2002 | Edwards et al. |
| 6,471,659 B2 | 10/2002 | Eggers et al. |
| 6,480,796 B2 | 11/2002 | Wiener |
| 6,537,272 B2 | 3/2003 | Christopherson et al. |
| 6,537,291 B2 | 3/2003 | Friedman et al. |
| 6,562,034 B2 | 5/2003 | Edwards et al. |
| 6,588,277 B2 | 7/2003 | Giordano et al. |
| 6,602,227 B1 | 8/2003 | Cimino et al. |
| 6,623,423 B2 | 9/2003 | Sakurai et al. |
| 6,626,926 B2 | 9/2003 | Friedman et al. |
| 6,633,234 B2 | 10/2003 | Wiener et al. |
| 6,662,127 B2 | 12/2003 | Wiener et al. |
| 6,678,621 B2 | 1/2004 | Wiener et al. |
| 6,679,899 B2 | 1/2004 | Wiener et al. |
| 6,712,074 B2 | 3/2004 | Edwards et al. |
| 6,736,810 B2 | 5/2004 | Hoey et al. |
| 6,740,079 B1 | 5/2004 | Eggers et al. |
| 6,740,085 B2 | 5/2004 | Hareyama et al. |
| 6,756,909 B2 | 6/2004 | Wiener et al. |
| 6,783,523 B2 | 8/2004 | Qin et al. |
| 6,809,508 B2 | 10/2004 | Donofrio |
| 6,849,073 B2 | 2/2005 | Hoey et al. |
| 6,872,206 B2 | 3/2005 | Edwards et al. |
| 6,898,536 B2 | 5/2005 | Wiener et al. |
| 6,923,804 B2 | 8/2005 | Eggers et al. |
| 6,923,809 B2 | 8/2005 | Eggers et al. |
| 6,945,981 B2 | 9/2005 | Donofrio et al. |
| 6,951,535 B2 | 10/2005 | Ghodoussi et al. |
| 6,955,653 B2 | 10/2005 | Eggers |
| 6,977,495 B2 | 12/2005 | Donofrio |
| 6,994,704 B2 | 2/2006 | Qin et al. |
| 7,004,174 B2 | 2/2006 | Eggers et al. |
| 7,041,096 B2 | 5/2006 | Malis et al. |
| 7,041,101 B2 | 5/2006 | Eggers |
| 7,063,692 B2 | 6/2006 | Sakurai et al. |
| 7,077,853 B2 | 7/2006 | Kramer et al. |
| 7,094,231 B1 | 8/2006 | Ellman et al. |
| 7,122,031 B2 | 10/2006 | Edwards et al. |
| 7,144,248 B2 | 12/2006 | Irwin |
| 7,169,144 B2 | 1/2007 | Hoey et al. |
| 7,179,271 B2 | 2/2007 | Friedman et al. |
| 7,217,269 B2 | 5/2007 | El-Galley et al. |
| 7,226,447 B2 | 6/2007 | Uchida et al. |
| 7,244,262 B2 | 7/2007 | Wiener et al. |
| 7,247,155 B2 | 7/2007 | Hoey et al. |
| 7,247,161 B2 | 7/2007 | Johnston et al. |
| 7,259,340 B2 * | 8/2007 | Blaha ................. H01H 9/182 200/310 |
| 7,273,483 B2 | 9/2007 | Wiener et al. |
| 7,302,288 B1 | 11/2007 | Schellengberg |
| 7,353,068 B2 | 4/2008 | Tanaka et al. |
| 7,375,644 B2 | 5/2008 | Miyazawa |
| 7,416,539 B2 | 8/2008 | Johnston et al. |
| 7,422,582 B2 | 9/2008 | Malackowski et al. |
| 7,443,296 B2 | 10/2008 | Mezhinsky et al. |
| 7,458,970 B2 | 12/2008 | Miura |
| 7,462,187 B2 | 12/2008 | Johnston et al. |
| 7,473,263 B2 | 1/2009 | Johnston et al. |
| 7,494,473 B2 | 2/2009 | Eggers et al. |
| 7,507,234 B2 | 3/2009 | Utley et al. |
| 7,507,238 B2 | 3/2009 | Edwards et al. |

(56) References Cited

U.S. PATENT DOCUMENTS

| | | |
|---|---|---|
| 7,551,077 B2 | 6/2009 | Raybuck et al. |
| 7,556,628 B2 | 7/2009 | Utley et al. |
| 7,557,317 B2 | 7/2009 | Blaha et al. |
| 7,569,053 B2 | 8/2009 | Eggers et al. |
| 7,594,925 B2 | 9/2009 | Danek et al. |
| 7,632,268 B2 | 12/2009 | Edwards et al. |
| 7,674,261 B2 | 3/2010 | Garito et al. |
| 7,675,430 B2 | 3/2010 | Warner et al. |
| 7,691,097 B2 | 4/2010 | Miyazawa |
| 7,708,768 B2 | 5/2010 | Danek et al. |
| 7,781,941 B2 | 8/2010 | Horvath et al. |
| 7,796,040 B2 | 9/2010 | Mezhinsky et al. |
| 7,799,044 B2 | 9/2010 | Johnston et al. |
| 7,828,797 B2 | 11/2010 | Eggers |
| 7,846,150 B2 | 12/2010 | Hamel et al. |
| 7,846,156 B2 | 12/2010 | Malis et al. |
| 7,883,031 B2 | 2/2011 | Collins, Jr. et al. |
| 7,883,458 B2 | 2/2011 | Hamel |
| 7,883,465 B2 | 2/2011 | Donofrio et al. |
| 7,891,361 B2 | 2/2011 | Irwin |
| 7,922,715 B2 | 4/2011 | Qin et al. |
| 7,981,109 B2 | 7/2011 | Avanzino et al. |
| 7,991,118 B2 | 8/2011 | Noordhoek |
| 8,012,136 B2 | 9/2011 | Collins, Jr. et al. |
| 8,058,771 B2 | 11/2011 | Giordano et al. |
| 8,083,735 B2 | 12/2011 | Morris |
| 8,109,903 B2 | 2/2012 | Ferliuc et al. |
| 8,149,108 B2 | 4/2012 | Hamel et al. |
| 8,216,233 B2 | 7/2012 | McClurken et al. |
| 8,231,553 B2 | 7/2012 | Joseph et al. |
| 8,235,917 B2 | 8/2012 | Joseph et al. |
| 8,241,271 B2 | 8/2012 | Millman et al. |
| 8,253,303 B2 | 8/2012 | Giordano et al. |
| 8,257,346 B2 | 9/2012 | Qin et al. |
| 8,274,376 B2 | 9/2012 | Shields et al. |
| 8,287,530 B2 | 10/2012 | Morris |
| 8,292,882 B2 | 10/2012 | Danek et al. |
| 8,298,224 B2 | 10/2012 | Danek et al. |
| 8,317,703 B2 | 11/2012 | Brannan |
| 8,348,946 B2 | 1/2013 | McClurken et al. |
| 8,357,175 B2 | 1/2013 | Mark |
| 8,418,073 B2 | 4/2013 | Mohr et al. |
| 8,430,825 B2 | 4/2013 | Mark |
| 8,454,640 B2 | 6/2013 | Johnston et al. |
| 8,454,669 B2 | 6/2013 | Irwin |
| 8,460,327 B2 | 6/2013 | Mark et al. |
| 8,461,744 B2 | 6/2013 | Wiener et al. |
| 8,465,473 B2 | 6/2013 | Horvath |
| 8,480,569 B2 | 7/2013 | Terliuc et al. |
| 8,496,599 B2 | 7/2013 | Mark |
| 8,496,681 B2 | 7/2013 | Easley |
| 8,506,565 B2 | 8/2013 | DeCarlo |
| 8,527,094 B2 | 9/2013 | Kumar et al. |
| 8,529,468 B2 | 9/2013 | Hoffa et al. |
| 8,545,463 B2 | 10/2013 | Collins, Jr. et al. |
| 8,546,996 B2 | 10/2013 | Messerly et al. |
| 8,551,082 B2 | 10/2013 | Strul et al. |
| 8,551,088 B2 | 10/2013 | Falkenstein et al. |
| 8,562,598 B2 | 10/2013 | Falkenstein et al. |
| 8,568,411 B2 | 10/2013 | Falkenstein et al. |
| 8,579,894 B2 | 11/2013 | Falkenstein et al. |
| 8,636,664 B2 | 1/2014 | Brannan |
| 8,636,727 B2 | 1/2014 | Bissig et al. |
| 8,652,121 B2 | 2/2014 | Quick et al. |
| 8,657,841 B2 | 2/2014 | Mark |
| 8,663,220 B2 | 3/2014 | Wiener et al. |
| 8,680,412 B2 | 3/2014 | Horvath et al. |
| 8,696,650 B2 | 4/2014 | Quick et al. |
| 8,702,738 B2 | 4/2014 | Mark |
| 8,704,425 B2 | 4/2014 | Giordano et al. |
| 8,709,009 B2 | 4/2014 | Hamel |
| 8,727,970 B2 | 5/2014 | Terliuc et al. |
| 8,746,253 B2 | 6/2014 | Irwin |
| 8,749,116 B2 | 6/2014 | Messerly et al. |
| 8,749,188 B2 | 6/2014 | Tran et al. |
| 8,773,001 B2 | 7/2014 | Wiener et al. |
| 8,777,963 B2 | 7/2014 | Diamant et al. |
| 8,779,648 B2 | 7/2014 | Giordano et al. |
| 8,784,415 B2 | 7/2014 | Malackowski et al. |
| 8,845,632 B2 | 9/2014 | Qin et al. |
| 8,858,464 B2 | 10/2014 | Hoffa et al. |
| 8,870,861 B2 | 10/2014 | El-Galley et al. |
| 8,882,503 B2 | 11/2014 | Guaragno |
| 8,888,774 B2 | 11/2014 | Edwards et al. |
| 8,888,803 B2 | 11/2014 | Mark |
| 8,900,249 B2 | 12/2014 | Boukhny et al. |
| 8,906,010 B2 | 12/2014 | Edwards et al. |
| 8,915,910 B2 | 12/2014 | Falkenstein et al. |
| 8,936,021 B2 | 1/2015 | Collins, Jr. |
| 8,951,248 B2 | 2/2015 | Messerly et al. |
| 8,956,349 B2 | 2/2015 | Aldridge et al. |
| 8,986,302 B2 | 3/2015 | Aldridge et al. |
| 9,017,326 B2 | 4/2015 | DiNardo et al. |
| 9,028,518 B2 | 5/2015 | Mark |
| 9,035,741 B2 | 5/2015 | Hamel et al. |
| 9,039,681 B2 | 5/2015 | Wang et al. |
| 9,039,695 B2 | 5/2015 | Giordano et al. |
| 9,050,093 B2 | 6/2015 | Aldridge et al. |
| 9,060,775 B2 | 6/2015 | Wiener et al. |
| 9,060,776 B2 | 6/2015 | Yates et al. |
| 9,072,539 B2 | 7/2015 | Messerly et al. |
| 9,084,623 B2 | 7/2015 | Gomez et al. |
| 9,089,256 B2 | 7/2015 | Tognaccini et al. |
| 9,089,360 B2 | 7/2015 | Messerly et al. |
| 9,101,397 B2 | 8/2015 | Guthart et al. |
| 9,119,623 B2 | 9/2015 | Malis et al. |
| 9,168,054 B2 | 10/2015 | Turner et al. |
| 9,168,091 B2 | 10/2015 | Janssen et al. |
| 9,192,441 B2 | 11/2015 | Brannan |
| 9,198,705 B2 | 12/2015 | Qin et al. |
| 9,199,091 B2 | 12/2015 | Danek et al. |
| 9,204,921 B2 | 12/2015 | Sisken |
| 9,216,031 B2 | 12/2015 | Mark et al. |
| 9,216,243 B2 | 12/2015 | Millman et al. |
| 9,226,766 B2 | 1/2016 | Aldridge et al. |
| 9,226,767 B2 | 1/2016 | Stulen et al. |
| 9,227,088 B2 | 1/2016 | Hissong et al. |
| 9,232,984 B2 | 1/2016 | Guthart et al. |
| 9,237,921 B2 | 1/2016 | Messerly et al. |
| 9,241,731 B2 | 1/2016 | Boudreaux et al. |
| 9,265,518 B2 | 2/2016 | Ware et al. |
| 9,265,581 B2 | 2/2016 | Navve et al. |
| 9,271,797 B2 | 3/2016 | Adler et al. |
| 9,271,798 B2 | 3/2016 | Kumar et al. |
| 9,279,751 B2 | 3/2016 | Mark et al. |
| 9,283,031 B2 | 3/2016 | Janssen et al. |
| 9,289,258 B2 | 3/2016 | Cohen |
| 9,326,788 B2 | 5/2016 | Batross et al. |
| 9,358,063 B2 | 6/2016 | Marion |
| 9,364,277 B2 | 6/2016 | Sisken et al. |
| 9,381,113 B2 | 7/2016 | Easley |
| 9,393,037 B2 | 7/2016 | Olson et al. |
| 9,439,668 B2 | 9/2016 | Timm et al. |
| 11,337,765 B2 | 5/2022 | Mintz et al. |
| 2002/0049551 A1 | 4/2002 | Friedman et al. |
| 2002/0156466 A1 | 10/2002 | Sakurai et al. |
| 2003/0178488 A1 | 9/2003 | Southard |
| 2003/0199085 A1 | 10/2003 | Berger et al. |
| 2004/0267297 A1 | 12/2004 | Malackowski |
| 2005/0004559 A1 | 1/2005 | Quick et al. |
| 2005/0021020 A1 | 1/2005 | Blaha |
| 2005/0033271 A1 | 2/2005 | Qin et al. |
| 2005/0062238 A1 | 3/2005 | Broadfield et al. |
| 2005/0107829 A1 | 5/2005 | Edwards et al. |
| 2005/0131436 A1 | 6/2005 | Johnston et al. |
| 2005/0267455 A1 | 12/2005 | Eggers et al. |
| 2005/0283148 A1 | 12/2005 | Janssen et al. |
| 2006/0074405 A1 | 4/2006 | Malackowski et al. |
| 2006/0129140 A1 | 6/2006 | Todd et al. |
| 2006/0181285 A1 | 8/2006 | Friedman et al. |
| 2006/0205999 A1 | 9/2006 | Berger et al. |
| 2006/0282064 A1 | 12/2006 | Shimizu et al. |
| 2007/0005002 A1 | 1/2007 | Millman et al. |
| 2007/0156121 A1 | 7/2007 | Millman et al. |

(56) References Cited

U.S. PATENT DOCUMENTS

| | | |
|---|---|---|
| 2007/0166662 A1 | 7/2007 | Lint et al. |
| 2007/0167943 A1 | 7/2007 | Janssen et al. |
| 2007/0208333 A1 | 9/2007 | Uchida et al. |
| 2007/0250098 A1* | 10/2007 | Malackowski ......... A61B 17/14 318/255 |
| 2008/0015563 A1 | 1/2008 | Hoey et al. |
| 2008/0015620 A1 | 1/2008 | Friedman et al. |
| 2008/0020714 A1* | 1/2008 | Mezhinsky ............ A61B 90/90 455/73 |
| 2008/0039746 A1 | 2/2008 | Hissong et al. |
| 2008/0114389 A1 | 5/2008 | Johnston et al. |
| 2008/0125768 A1 | 5/2008 | Tahara et al. |
| 2008/0281318 A1 | 11/2008 | Herbette et al. |
| 2009/0099520 A1 | 4/2009 | Millman et al. |
| 2009/0114742 A1 | 5/2009 | Collins, Jr. |
| 2009/0118751 A1 | 5/2009 | Wiener et al. |
| 2009/0131929 A1 | 5/2009 | Shimizu |
| 2009/0212133 A1 | 8/2009 | Collins, Jr. |
| 2009/0254079 A1 | 10/2009 | Edwards et al. |
| 2009/0259223 A1 | 10/2009 | Eggers et al. |
| 2010/0063495 A1 | 3/2010 | Edwards et al. |
| 2010/0100082 A1 | 4/2010 | Shimizu et al. |
| 2010/0125292 A1 | 5/2010 | Wiener et al. |
| 2010/0152533 A1 | 6/2010 | Mark |
| 2010/0152762 A1 | 6/2010 | Mark |
| 2010/0198200 A1* | 8/2010 | Horvath ................ G05G 1/305 606/1 |
| 2010/0222752 A1 | 9/2010 | Collins, Jr. et al. |
| 2011/0112405 A1 | 5/2011 | Barthe et al. |
| 2011/0125149 A1 | 5/2011 | El-Galley et al. |
| 2011/0144636 A1 | 6/2011 | Alexander et al. |
| 2011/0224669 A1 | 9/2011 | Podany |
| 2012/0016239 A1 | 1/2012 | Barthe et al. |
| 2012/0029354 A1 | 2/2012 | Mark et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0064483 A1 | 3/2012 | Lint et al. |
| 2012/0078139 A1 | 3/2012 | Aldridge et al. |
| 2012/0078279 A1 | 3/2012 | Mark |
| 2012/0203168 A1 | 8/2012 | Fujimoto et al. |
| 2012/0277663 A1 | 11/2012 | Millman et al. |
| 2013/0023873 A1 | 1/2013 | Danek et al. |
| 2013/0030328 A1 | 1/2013 | Dycus et al. |
| 2013/0090641 A1 | 4/2013 | McKinney et al. |
| 2013/0116737 A1 | 5/2013 | Edwards et al. |
| 2013/0267975 A1 | 10/2013 | Timm et al. |
| 2013/0274727 A1 | 10/2013 | Lin |
| 2013/0296908 A1 | 11/2013 | Schulte et al. |
| 2013/0303904 A1 | 11/2013 | Barthe et al. |
| 2013/0303905 A1 | 11/2013 | Barthe et al. |
| 2013/0310641 A1 | 11/2013 | Terliuc et al. |
| 2014/0017629 A1 | 1/2014 | Lint et al. |
| 2014/0066927 A1 | 3/2014 | Brustad et al. |
| 2014/0074153 A1 | 3/2014 | Fujimoto et al. |
| 2014/0107538 A1 | 4/2014 | Wiener et al. |
| 2014/0155771 A1 | 6/2014 | Quick et al. |
| 2014/0207124 A1 | 7/2014 | Aldridge et al. |
| 2014/0235941 A1 | 8/2014 | Terliuc et al. |
| 2014/0257046 A1* | 9/2014 | Steven .................. A61B 90/90 600/301 |
| 2014/0266636 A1 | 9/2014 | Larsen et al. |
| 2014/0276055 A1 | 9/2014 | Barthe et al. |
| 2014/0288571 A1 | 9/2014 | Diamant et al. |
| 2014/0324039 A1 | 10/2014 | Malackowski et al. |
| 2014/0330332 A1 | 11/2014 | Danek et al. |
| 2014/0343369 A1 | 11/2014 | Nakamura et al. |
| 2015/0005622 A1 | 1/2015 | Zhao et al. |
| 2015/0011990 A1 | 1/2015 | Qin et al. |
| 2015/0031126 A1 | 1/2015 | Mark et al. |
| 2015/0032025 A1 | 1/2015 | Mark et al. |
| 2015/0051607 A1 | 2/2015 | Hajishah et al. |
| 2015/0057563 A1 | 2/2015 | Kowalski et al. |
| 2015/0094710 A1 | 4/2015 | Edwards et al. |
| 2015/0118636 A1 | 4/2015 | Guaragno |
| 2015/0133917 A1 | 5/2015 | Edwards et al. |
| 2015/0150639 A1 | 6/2015 | Diolaiti et al. |
| 2015/0182230 A1 | 7/2015 | Belagali et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0216513 A1 | 8/2015 | Hamel et al. |
| 2015/0217141 A1 | 8/2015 | Barthe et al. |
| 2015/0248847 A1 | 9/2015 | Wang et al. |
| 2015/0257814 A1* | 9/2015 | Berry .................... A61B 34/74 606/34 |
| 2015/0297282 A1 | 10/2015 | Cadouri |
| 2015/0297300 A1 | 10/2015 | Gomez et al. |
| 2015/0327883 A1 | 11/2015 | Messerly et al. |
| 2015/0327919 A1 | 11/2015 | Clopp et al. |
| 2015/0328484 A1 | 11/2015 | Messerly et al. |
| 2015/0340586 A1 | 11/2015 | Wiener et al. |
| 2015/0342677 A1 | 12/2015 | Chalfant |
| 2015/0366625 A1 | 12/2015 | Tognaccini et al. |
| 2015/0374333 A1 | 12/2015 | Barthe et al. |
| 2016/0015992 A1 | 1/2016 | Whitlock |
| 2016/0030663 A1 | 2/2016 | Adaniya et al. |
| 2016/0038230 A1 | 2/2016 | Danek et al. |
| 2016/0066944 A1 | 3/2016 | Mark et al. |
| 2016/0066984 A1 | 3/2016 | Janssen et al. |
| 2016/0089533 A1 | 3/2016 | Turner et al. |
| 2016/0120563 A1 | 5/2016 | Messerly et al. |
| 2016/0120603 A1 | 5/2016 | Grace et al. |
| 2016/0128678 A1 | 5/2016 | Ware et al. |
| 2016/0140875 A1 | 5/2016 | Kumar et al. |
| 2016/0157883 A1 | 6/2016 | Hissong et al. |
| 2016/0166345 A1 | 6/2016 | Kumar et al. |
| 2016/0192999 A1 | 7/2016 | Stulen et al. |
| 2016/0220300 A1 | 8/2016 | Cohen |
| 2019/0117322 A1 | 4/2019 | Laubenthal et al. |
| 2020/0188048 A1* | 6/2020 | Vokrot .................. A61B 34/35 |

FOREIGN PATENT DOCUMENTS

| | | |
|---|---|---|
| DE | 1123788 A1 | 1/1993 |
| DE | 10135155 A1 | 5/2002 |
| EP | 0424687 A1 | 5/1991 |
| EP | 0740370 A1 | 10/1996 |
| EP | 0933792 A1 | 8/1999 |
| EP | 1389788 A1 | 2/2004 |
| EP | 1410766 A1 | 4/2004 |
| EP | 1674039 A2 | 6/2006 |
| EP | 1787606 A1 | 5/2007 |
| EP | 1800705 A2 | 6/2007 |
| EP | 2392285 A1 | 12/2011 |
| JP | 2000106049 A | 4/2000 |
| WO | 95003740 A1 | 2/1995 |
| WO | 95020779 A1 | 8/1995 |
| WO | 9806338 A2 | 2/1998 |
| WO | 98008447 A1 | 3/1998 |
| WO | 98008448 A1 | 3/1998 |
| WO | 98008450 A1 | 3/1998 |
| WO | 98008451 A1 | 3/1998 |
| WO | 98008452 A1 | 3/1998 |
| WO | 98008453 A1 | 3/1998 |
| WO | 98033557 A1 | 8/1998 |
| WO | 99017672 A1 | 4/1999 |
| WO | 99038444 A1 | 8/1999 |
| WO | 2000066006 A1 | 11/2000 |
| WO | 2000066013 A1 | 11/2000 |
| WO | 2000066015 A1 | 11/2000 |
| WO | 2000066016 A1 | 11/2000 |
| WO | 2000066017 A1 | 11/2000 |
| WO | 2000066018 A1 | 11/2000 |
| WO | 2000066019 A1 | 11/2000 |
| WO | 2000066020 A1 | 11/2000 |
| WO | 2000066021 A1 | 11/2000 |
| WO | 2000066052 A1 | 11/2000 |
| WO | 2001017450 A1 | 3/2001 |
| WO | 2001017452 A1 | 3/2001 |
| WO | 2001028446 A1 | 4/2001 |
| WO | 2001047409 A1 | 7/2001 |

(56) References Cited

FOREIGN PATENT DOCUMENTS

| | | |
|---|---|---|
| WO | 2003005918 A1 | 1/2003 |
| WO | 2003007861 A1 | 1/2003 |
| WO | 2003047446 A1 | 6/2003 |
| WO | 2003079911 A1 | 10/2003 |
| WO | 2003088892 A2 | 10/2003 |
| WO | 2003105169 A1 | 12/2003 |
| WO | 2004007023 A1 | 1/2004 |
| WO | 2004017849 A1 | 3/2004 |
| WO | 2004030552 A1 | 4/2004 |
| WO | 2004088463 A2 | 10/2004 |
| WO | 2004103478 A1 | 12/2004 |
| WO | 2004107989 A1 | 12/2004 |
| WO | 2005011464 A2 | 2/2005 |
| WO | 2005011465 A2 | 2/2005 |
| WO | 2005011466 A2 | 2/2005 |
| WO | 2005011467 A2 | 2/2005 |
| WO | 2005043324 A2 | 5/2005 |
| WO | 2005060398 A2 | 7/2005 |
| WO | 2006009705 A2 | 1/2006 |
| WO | 2006039331 A2 | 4/2006 |
| WO | 2006050410 A1 | 5/2006 |
| WO | 2006116198 A2 | 11/2006 |
| WO | 2007012990 A2 | 2/2007 |
| WO | 2007084668 A2 | 7/2007 |
| WO | 2007106208 A2 | 9/2007 |
| WO | 2007135665 A2 | 11/2007 |
| WO | 2007140331 A2 | 12/2007 |
| WO | 2008011553 A2 | 1/2008 |
| WO | 2008014465 A2 | 1/2008 |
| WO | 2008016803 A2 | 2/2008 |
| WO | 2008094481 A2 | 8/2008 |
| WO | 2008098085 A2 | 8/2008 |
| WO | 2008118777 A2 | 10/2008 |
| WO | 2008142685 A2 | 11/2008 |
| WO | 2008143690 A2 | 11/2008 |
| WO | 2009005656 A2 | 1/2009 |
| WO | 2009023408 A1 | 2/2009 |
| WO | 2009064346 A1 | 5/2009 |
| WO | 2009105488 A2 | 8/2009 |
| WO | 2009124097 A1 | 10/2009 |
| WO | 2009137421 A1 | 11/2009 |
| WO | 2009149390 A1 | 12/2009 |
| WO | 2010017149 A1 | 2/2010 |
| WO | 2010047703 A2 | 4/2010 |
| WO | 2010057179 A2 | 5/2010 |
| WO | 2010077931 A2 | 7/2010 |
| WO | 2010078428 A1 | 7/2010 |
| WO | 2010096139 A2 | 8/2010 |
| WO | 2010128994 A1 | 11/2010 |
| WO | 2011002701 A1 | 1/2011 |
| WO | 2011008672 A2 | 1/2011 |
| WO | 2011044338 A2 | 4/2011 |
| WO | 2011112991 A1 | 9/2011 |
| WO | 2011146682 A1 | 11/2011 |
| WO | 2012044600 A2 | 4/2012 |
| WO | 2012122389 A1 | 9/2012 |
| WO | 2012162483 A1 | 11/2012 |
| WO | 2012170379 A1 | 12/2012 |
| WO | 2013048912 A2 | 4/2013 |
| WO | 2013052815 A1 | 4/2013 |
| WO | 2013052963 A1 | 4/2013 |
| WO | 2013134133 A1 | 9/2013 |
| WO | 2013154919 A2 | 10/2013 |
| WO | 2013154921 A2 | 10/2013 |
| WO | 2013154923 A2 | 10/2013 |
| WO | 2013154924 A1 | 10/2013 |
| WO | 2013154925 A2 | 10/2013 |
| WO | 2013158537 A2 | 10/2013 |
| WO | 2013177423 A2 | 11/2013 |
| WO | 2014004113 A2 | 1/2014 |
| WO | 2014004115 A1 | 1/2014 |
| WO | 2014004116 A1 | 1/2014 |
| WO | 2014093603 A1 | 6/2014 |
| WO | 2014116481 A1 | 7/2014 |
| WO | 2014145548 A2 | 9/2014 |
| WO | 2014176052 A1 | 10/2014 |
| WO | 2015002744 A1 | 1/2015 |
| WO | 2015024105 A1 | 2/2015 |
| WO | 2015167623 A2 | 11/2015 |
| WO | 2015175177 A2 | 11/2015 |
| WO | 2016008041 A1 | 1/2016 |
| WO | 2016011398 A1 | 1/2016 |
| WO | 2016049180 A1 | 3/2016 |
| WO | 2016073369 A1 | 5/2016 |
| WO | 2016081700 A1 | 5/2016 |

OTHER PUBLICATIONS

English language abstract and machine-assisted English translation for DE 101 35 155 extracted from google patent database on Mar. 7, 2019 (original document not available), 11 pages.

English language abstract and machine-assisted English translation for DE 41 23 788 extracted from espacenet.com database on Aug. 27, 2020, 6 pages.

English language abstract and machine-assisted English translation for EP 1 410 766 extracted from google patents database on Mar. 7, 2019, 10 pages.

English language abstract and machine-assisted English translation for JP 2000-106049 extracted from espacenet. com database on Aug. 27, 2020, 11 pages.

International Search Report for Application No. PCT/US2018/029914 dated Jul. 12, 2018, 3 pages.

STRYKER, "CORE—Consolidated Operating Room Equipment Powered Instrument Driver REF 5400-050-000 Instructions for Use", Software Version 8.x, Rev. L (5400-050-700), Jun. 2015, 47 pages.

Mann, Erica., "K171840", XP093032362, https://www.accessdata.fda.gov/cdrh_docs/pdf17/K171840.pdf, Sep. 15, 2017, 7 pages.

English language abstract for CN 101321606 A extracted from espacenet.com database on Nov. 3, 2022, 2 pages.

* cited by examiner

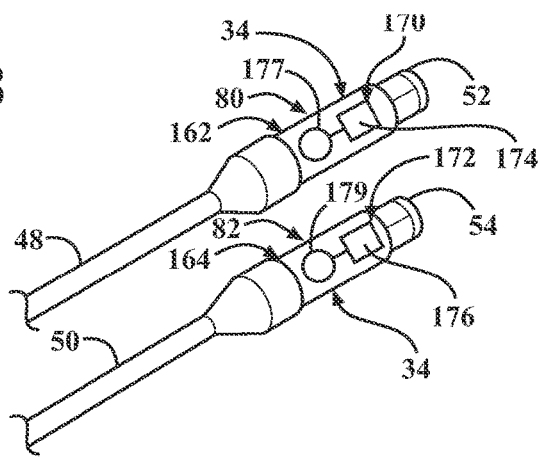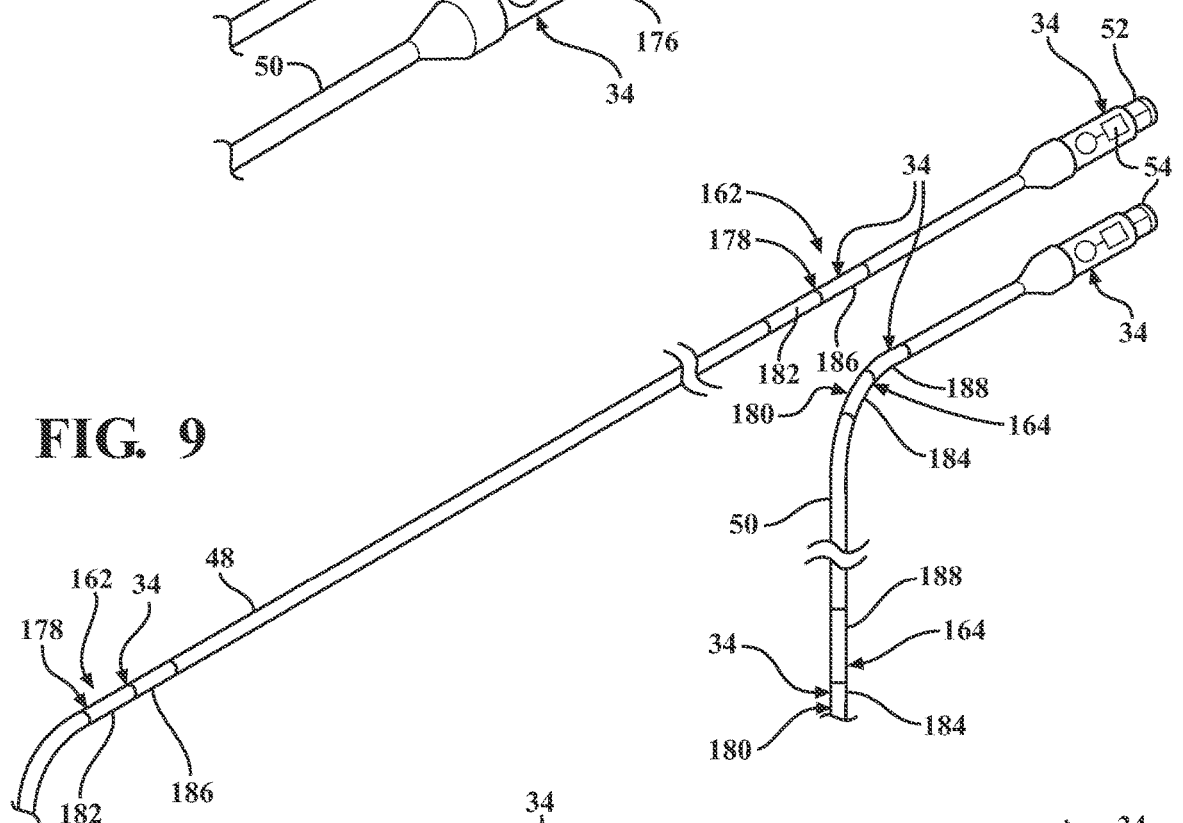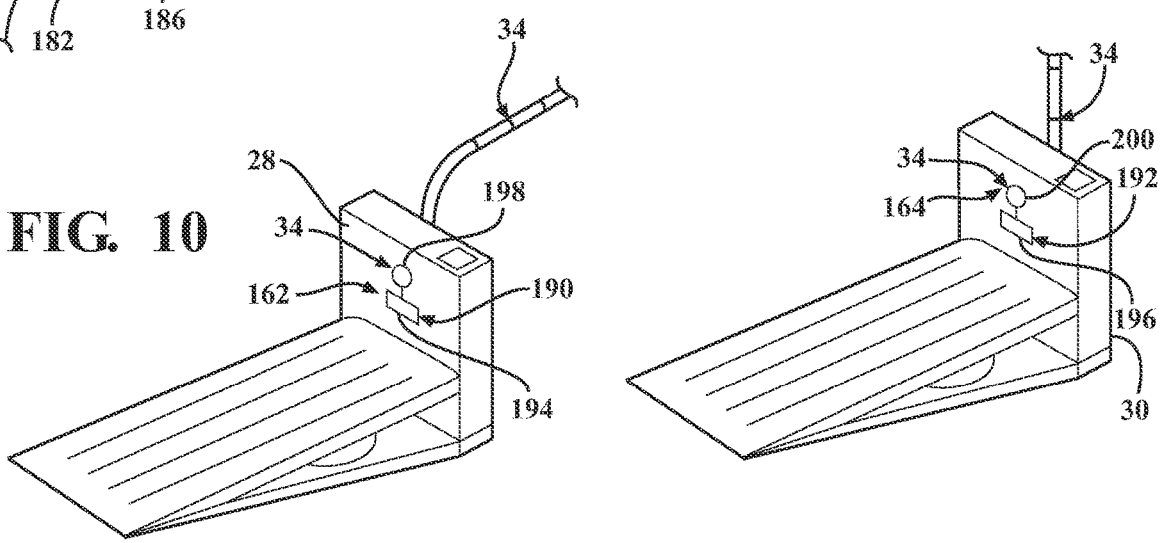

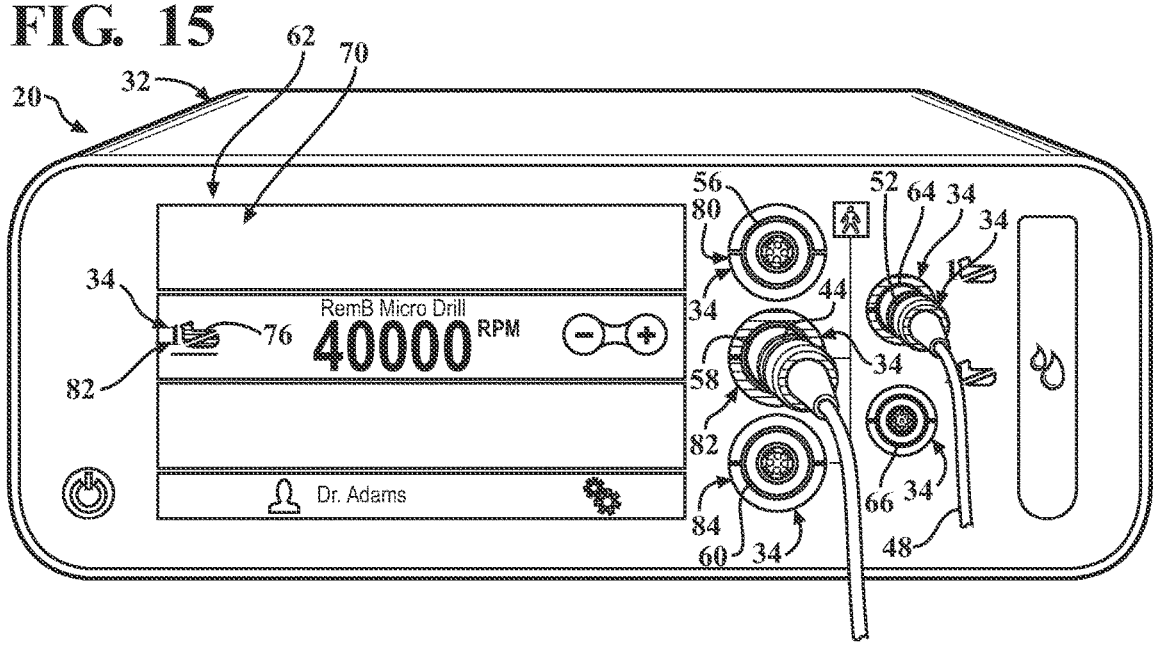
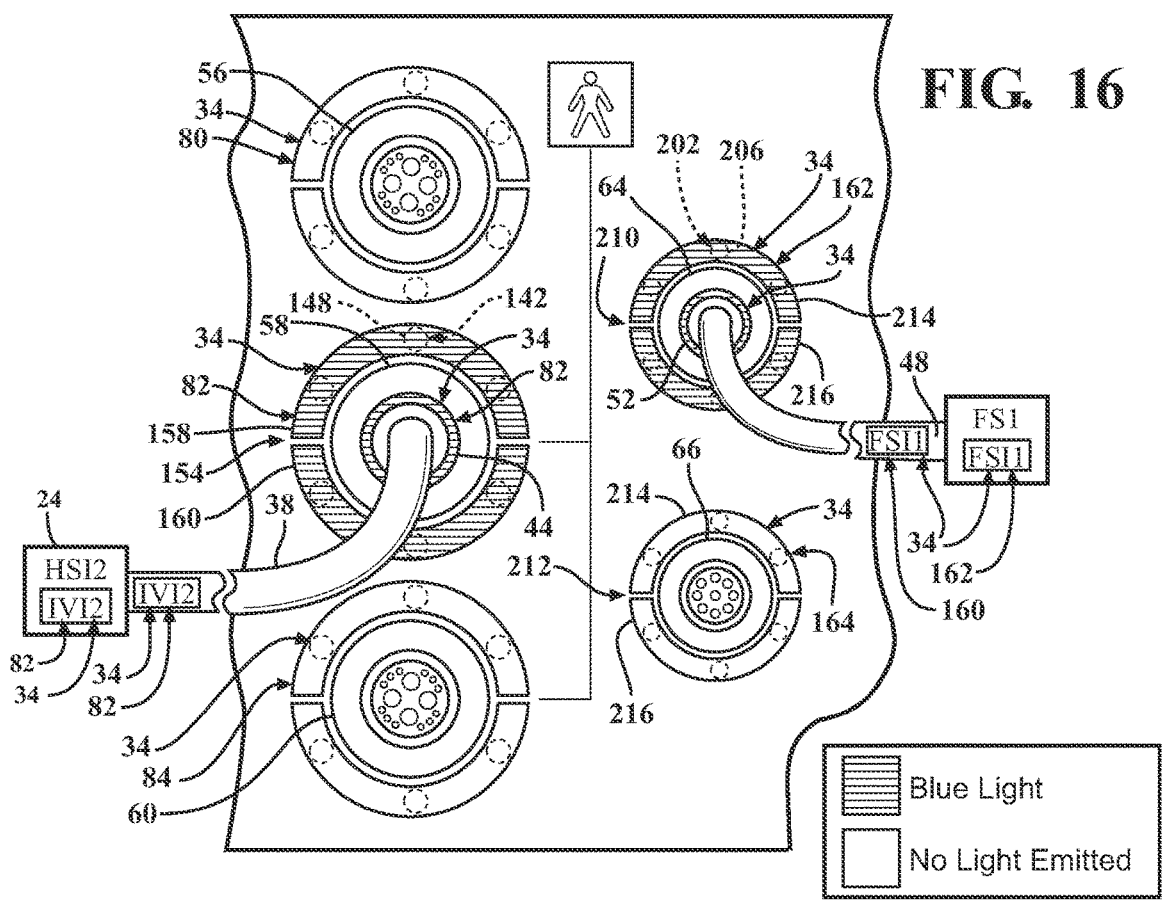

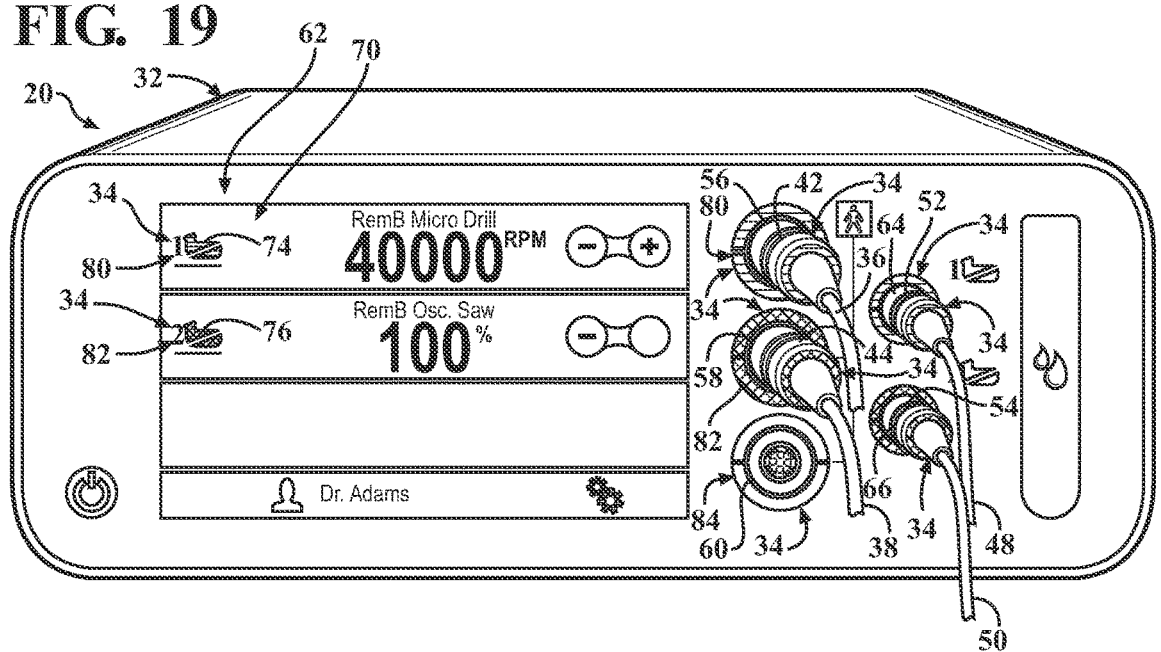
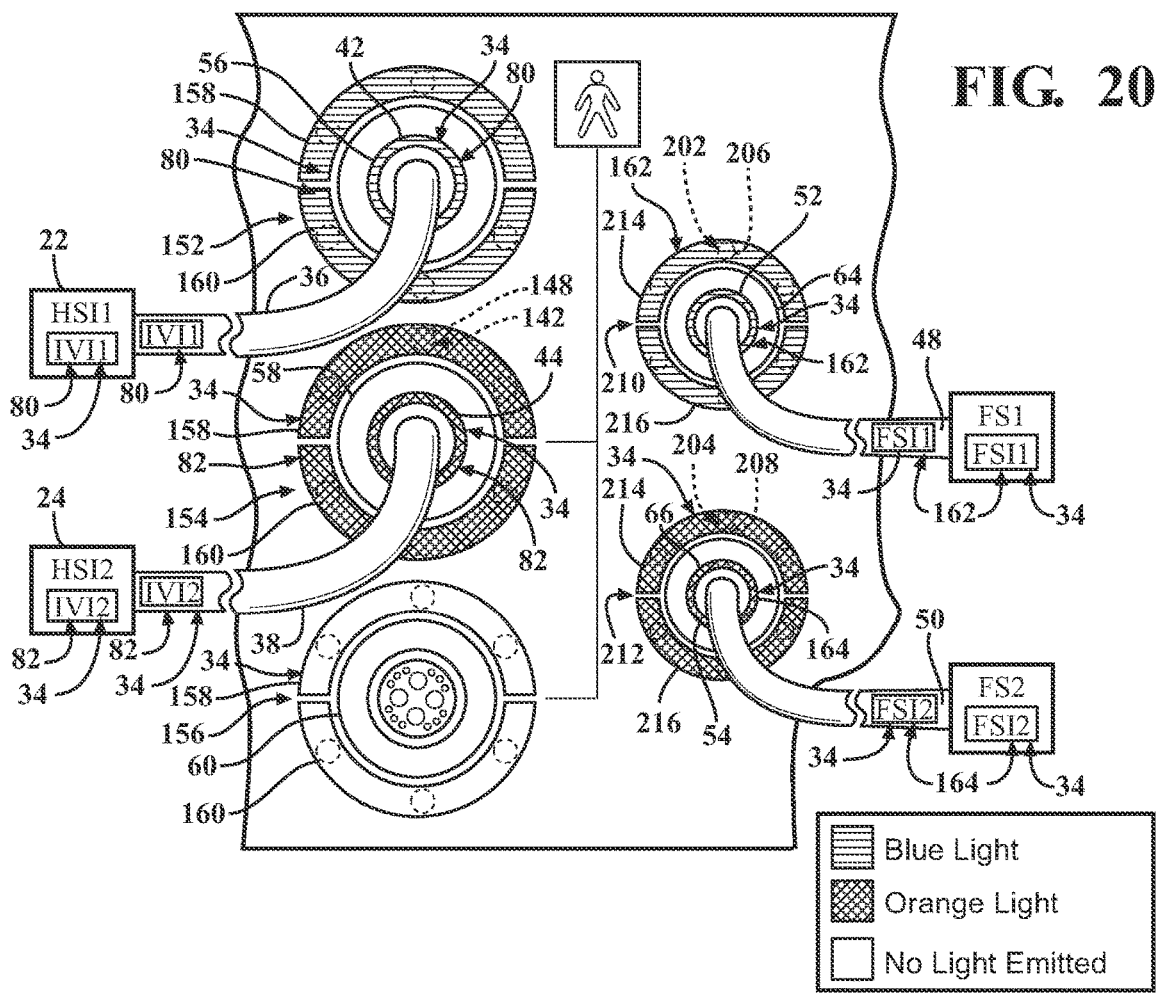

SYSTEM AND METHOD FOR INDICATING MAPPING OF CONSOLE-BASED SURGICAL SYSTEMS

CROSS-REFERENCE TO RELATED APPLICATION

This application is a continuation of U.S. patent application Ser. No. 16/220,542, filed on Dec. 14, 2018, which is a continuation-in-part of PCT International Application No. PCT/US2018/029914, filed Apr. 27, 2018, which claims the benefit of U.S. Provisional Patent Application No. 62/491,668, filed Apr. 28, 2017, all of which are hereby incorporated by reference in their entireties.

TECHNICAL FIELD

This disclosure is related to a console-based surgical system and method for associating handheld surgical instruments with input devices and activating visual indicators to indicate the instruments and input devices that are associated with one another.

SUMMARY OF THE DISCLOSURE

One embodiment of this disclosure relates to a new and useful console-based surgical system that associates handheld surgical instruments with input devices and activates visual indicators to indicate the instruments and input devices that are associated with one another. The system comprises a plurality of handheld surgical instruments, each instrument having a connector line and at least one of said plurality of handheld surgical instruments comprising an instrument visual indicator. The system further comprises a footswitch having a connector line and comprising a footswitch visual indicator. The system further comprises a console, which in turn comprises a plurality of instrument ports, with the connector lines of the handheld instruments being connected to the instrument ports. The console further comprises a footswitch port, with the connector line of the footswitch connected to the footswitch port. The console further comprises a controller configured to associate the footswitch port with one of the instrument ports such that the footswitch is operable to actuate a function of the handheld surgical instrument connected to the associated instrument port. The controller is further configured to activate the footswitch visual indicator and the instrument visual indicator of the associated instrument port to display outputs that correspond with one another.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination within one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows:

FIG. 8 is an enlarged view of first and second footswitch plugs capable of being connected to the first and second footswitch ports of the console shown in FIG. 1, with the first and second footswitch plugs comprising first and second footswitch visual indicators.

FIG. 9 is an enlarged view of first and second connector lines for the first and second footswitches shown in FIG. 1, with the first and second connector lines comprising first and second footswitch visual indicators.

FIG. 10 is an enlarged view of the first and second footswitches shown in FIG. 1, illustrating the first and second footswitches comprising first and second footswitch visual indicators.

FIG. 15 is a front perspective view of the console of FIG. 3, illustrating the second connector line of the second handheld surgical instrument coupled to the second instrument port and the second connector line of the first footswitch coupled to the first footswitch port.

FIG. 16 is an enlarged view of the instrument ports and footswitch ports of FIG. 15, with an association between the second instrument port and the first footswitch port being indicated by a plurality of second instrument visual indicators and a plurality of first footswitch visual indicators.

FIG. 19 is a front perspective view of the console of FIG. 13, further illustrating the connector line of the second handheld surgical instrument coupled to the second instrument port and the connector line of the second footswitch coupled to the second footswitch port.

FIG. 20 is an enlarged view of the instrument ports and footswitch ports of FIG. 14, further including an association between the second instrument port and the second footswitch port indicated by a plurality of second instrument visual indicators and a plurality of second footswitch visual indicators.

DETAILED DESCRIPTION

Figure 1:
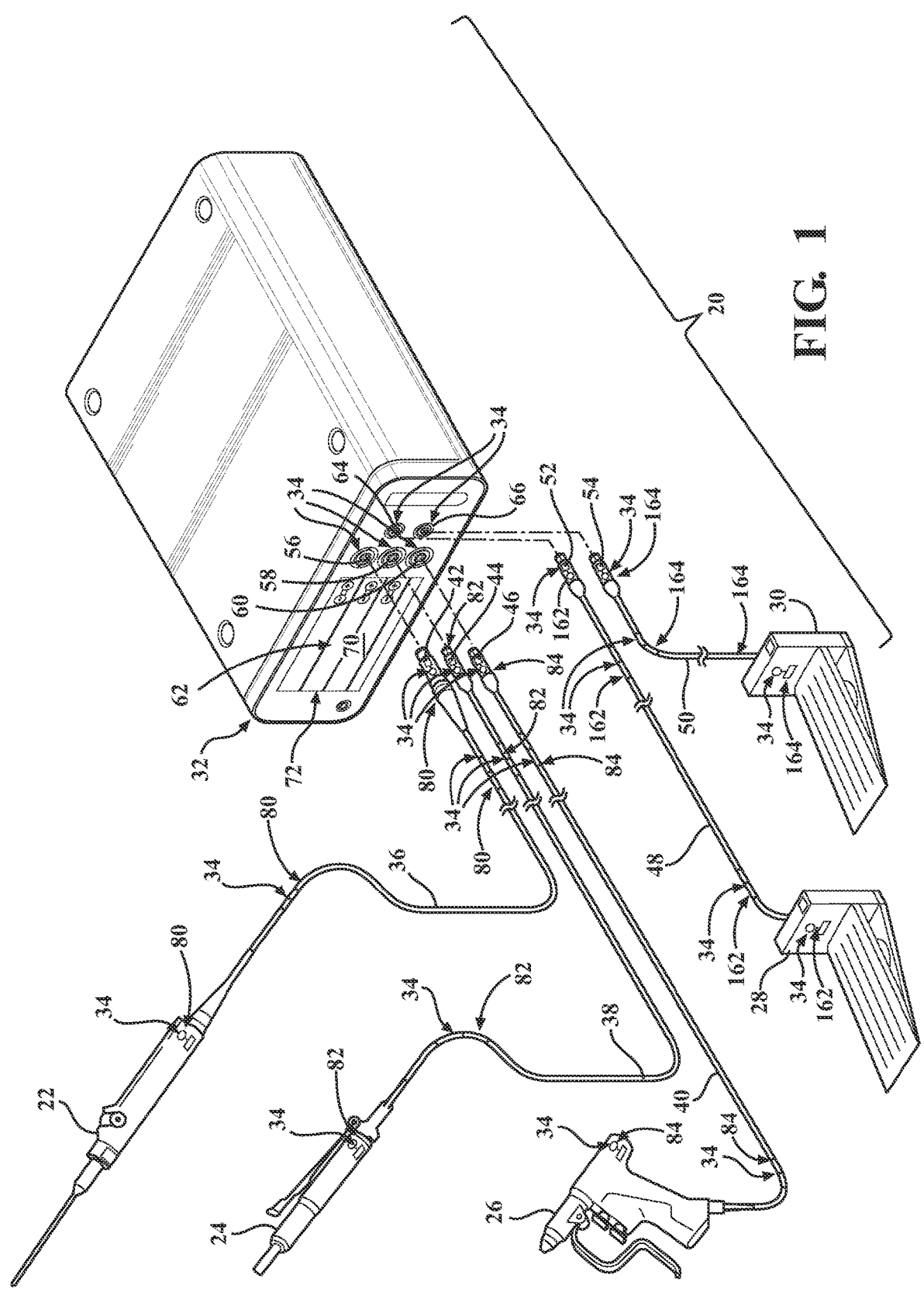
FIG. 1 is an exploded view of a console-based surgical system comprising a console, a plurality of handheld surgical instruments, and a plurality of input devices.

Referring to FIG. 1, a console-based surgical system 20 may comprise first, second, and third handheld surgical instruments 22, 24, 26, first and second footswitches 28, 30, and a console 32 for associating one or more of the instruments 22, 24, 26 with one or more of the footswitches 28, 30 to control the associated instruments during a surgical procedure. The system 20 further comprises a plurality of visual indicators 34 for indicating which of the instruments 22, 24, 26 and footswitches 28, 30 correspond with one another. The system 20 is shown in FIG. 1 as, for exemplary purposes, controlling three handheld surgical instruments 22, 24, 26, but in other embodiments, the system can control one, two, four, five, or any suitable number and type of instruments. Furthermore, system 20 is shown as, for exemplary purposes, comprising two footswitches 28, 30, but in other embodiments, the system may comprise one, three, four, five, or any number of footswitches or other types of input devices. The system 20 is also shown as, for exemplary purposes, comprising twenty-five (25) visual indicators 34, but in other embodiments any number of visual indicators may be used to indicate the association between the instrument ports and footswitch ports. An illustrative embodiment of an exemplary footswitch, which may be used as footswitches 28 and/or 30, is described below with reference to FIGS. 25-28.

Each one of the first, second, and third handheld surgical instruments 22, 24, 26 is configured to perform one or more predetermined functions in the treatment or care of a patient. Each instrument 22, 24, 26 can utilize one or more components that require electricity. As one example, one or more of the instruments may comprise a specialty drill such as one sold under the brand name CORE UNIVERSAL SERIES by Stryker Instruments of Kalamazoo, Mich., United States. Other examples of the instruments may comprise: a high-powered tapered drill, such as one sold under the brand name CORE SUMEX DRILL by Stryker Instruments; a modular handpiece such as one sold under the brand name CORE UNIVERSAL DRIVER by Stryker Instruments; a high-speed pencil-grip drill such as one sold under the brand name CORE MICRO DRILL by Stryker; a pneumatic drill such as one sold under the brand name MAESTRO DRILL by Stryker; a drill for intraoperative procedures such as one sold under the brand name ARIA MRI DRILL SYSTEM by Stryker; a drill for oral surgery such as one sold under the brand name CORE IMPACTION DRILL by Stryker; a drill for ENT surgery sold under the brand name SABER DRILL by Stryker; a sagittal saw, an oscillating saw, or a reciprocating saw, such as those sold under the brand name MICRO SAW by Stryker; various burs for small bone procedures such as those sold under the brand names ELITE BUR, ZYPHR BUR, MIS BUR, and TPS BUR; a microdebrider such as one sold under the brand name ESSX MICRODE-BRIDER; an ultrasonic aspirator such as one sold under the brand name SONOPET ULTRASONIC ASPIRATOR by Stryker; a pair of bipolar forceps such as one sold under the brand name SILVERGLIDE BIPOLAR FORCEPS by Stryker.

Other handheld surgical instruments sold by Stryker or any manufacturer are also contemplated. For instance, electrosurgical devices, ultrasound devices, and other surgical devices may also be employed. Electrosurgical instruments and others like them can be of any suitable type known in the art, including those that use diathermy with either unipolar or bipolar current (commonly referred to simply as unipolar devices and bipolar devices), and advanced devices such as harmonic scissors and argon beam and laser devices. The illustrated shapes and other structural features of instruments 22, 24, 26 as depicted in FIG. 1 are not intended to describe the instruments specifically but rather are intended only to convey the general concept that various instruments can be used. Indeed, it is important to note that the present disclosure facilitates the integration of instruments that may have different functions and other characteristics in terms of how they respond to their associated device user controls (not shown) and in terms of the signals produced by their device user controls that characterize their operation. For example, the instruments 22, 24, 26 can have functions that differ from those of each other as a result of the first handheld surgical instrument 22 being, for example, a unipolar device, while second handheld surgical instrument 24 is, for example, a bipolar device, and the third handheld surgical instrument 26 is a harmonic device. In addition, it may be that, for example, the first and second handheld surgical instruments 22 and 24 have different operating characteristics from each other because they require signals of different voltages from each other. The various devices may be produced by different manufacturers or be different versions or models of a device. Regardless of any such differences, the system 20 ensures that any and all of the instruments to which it is connected can be controlled by the first and second footswitches 28, 30 or the console 32.

Additionally, while handheld surgical instruments are emphasized in this disclosure, other types of medical devices may also be used in place thereof in certain embodiments. For example, suitable medical devices that could be used in conjunction with the console, include, but are not limited to, patient therapy devices, patient monitoring devices, or surgical instruments that are not handheld, such as surgical robots, hospital beds, lighting systems, cameras, etc. As such, the term "handheld surgical instrument" may be interchanged with these medical devices throughout this disclosure.

The first, second, and third handheld surgical instruments 22, 24, 26 may comprise a corresponding one of connector lines 36, 38, 40. Each connector line 36, 38, 40 may terminate at one end that is coupled to a corresponding one of the instruments 22, 24, 26 and terminate at an opposing end with a corresponding one of plugs 42, 44, 46 configured to engage the console 32 as provided in the description below for FIGS. 13-24. In other embodiments, the connector lines may terminate with a socket or any type of connector.

In the illustrated embodiment, footswitch 28 and/or footswitch 30 can comprise a footswitch sold under the brand name UNI-DIRECTIONAL FOOTSWITCH by Stryker, a footswitch sold under the brand name TPS FOOTSWITCH by Stryker, or any other type of input device sold by Stryker or another manufacturer. For example, the input device may be integral with the handheld surgical instruments, or may take the form of handswitches, voice-actuated switches, knee switches, or other types of switches that can be actuated by a user. Each input device may include one or more sensors, such as Hall effect sensors, magnetic sensors, or other suitable sensors, that generate signals in response to depression of the input device, such as the footswitch. As such, the term "footswitch" may be interchanged throughout this disclosure for input device.

The footswitches 28, 30 may comprise a corresponding one of connector lines 48, 50. Each connector line 48, 50 may terminate at one end that is coupled to a corresponding one of the footswitches 28, 30 and terminate at an opposing end with a corresponding one of plugs 52, 54 configured to engage the console 32 as provided in the description below for FIGS. 13-24. In other embodiments, the connector lines may terminate with a socket or any type of connector.

Figure 3:
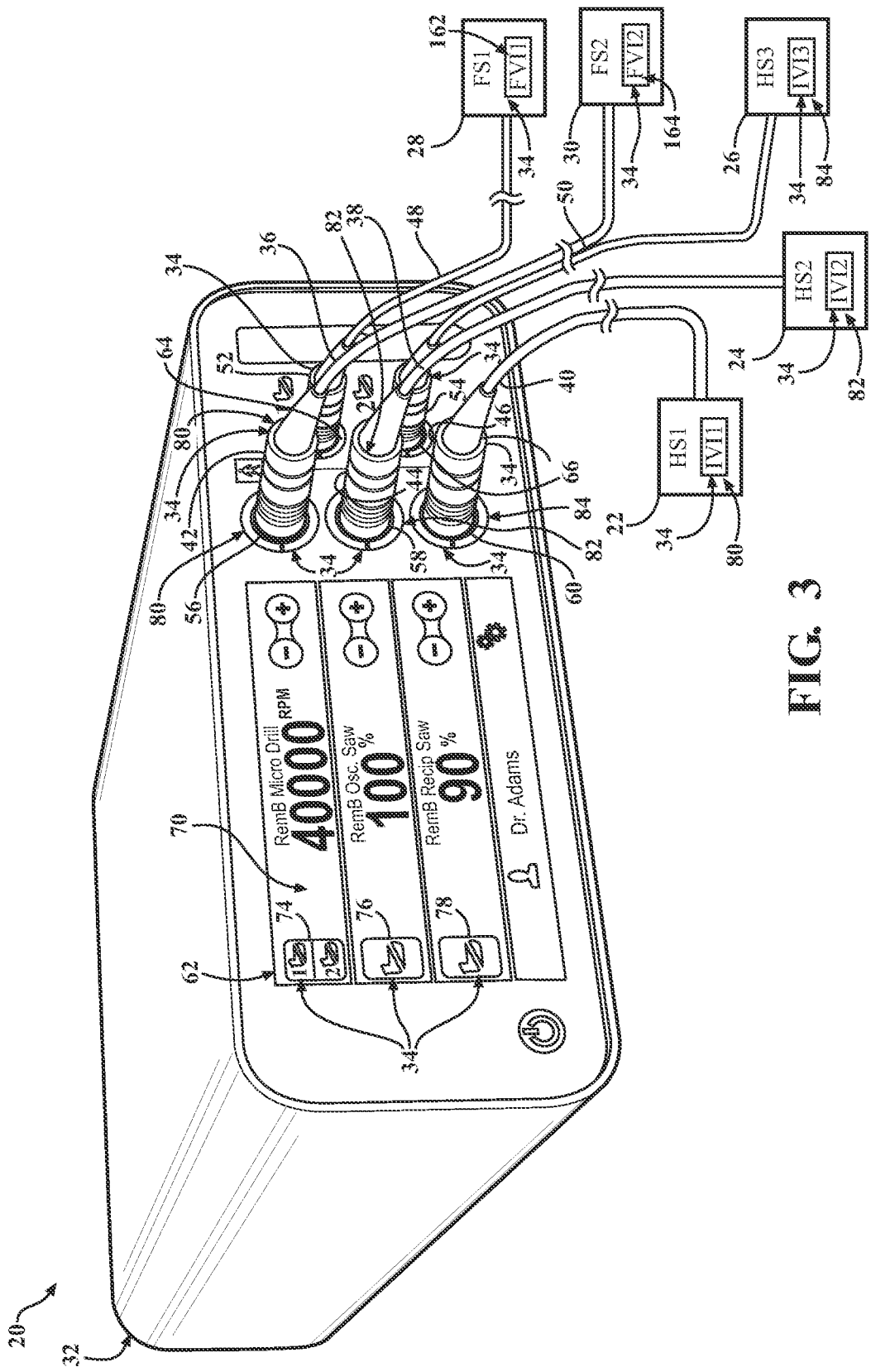
FIG. 3 is an enlarged perspective view of the console of FIG. 1, illustrating the console having a first instrument port, a second instrument port, a third instrument port, a first footswitch port, and a second footswitch port, which are respectively able to be operably coupled to the first handheld surgical instrument, the second handheld surgical instrument, the third handheld surgical instrument, the first footswitch, and the second footswitch.

The console 32 comprises first, second, and third instrument ports 56, 58, 60. The plugs 42, 44, 46 of the connector lines 36, 38, 40 associated with the handheld surgical instruments 22, 24, 26 are capable of being connected to a corresponding one of the first, second, and third instrument ports 56, 58, 60. While FIG. 3 illustrates that the console 32 has a display 62 with the first, second, and third instrument ports 56, 58, 60 positioned adjacent to the display 62, it is contemplated that the system 20 can instead comprise one, two, four, or any number of instrument ports positioned on any suitable portion of the console 32. Furthermore, the console 32 comprises first and second footswitch ports 64, 66. The plugs 52, 54 of the connector lines 48, 50 associated with the footswitches 28, 30 are capable of being connected to the first and second footswitch ports 64, 66. The first and second footswitch ports 64, 66 are spaced apart from the display 62, such that the first, second, and third instrument ports 56, 58, 60 are positioned between the footswitch ports 64, 66 and the display 62. However, other configurations of the instrument ports 56, 58, 60, the footswitch ports 64, 66, and the display 62 are contemplated.

Figure 2:
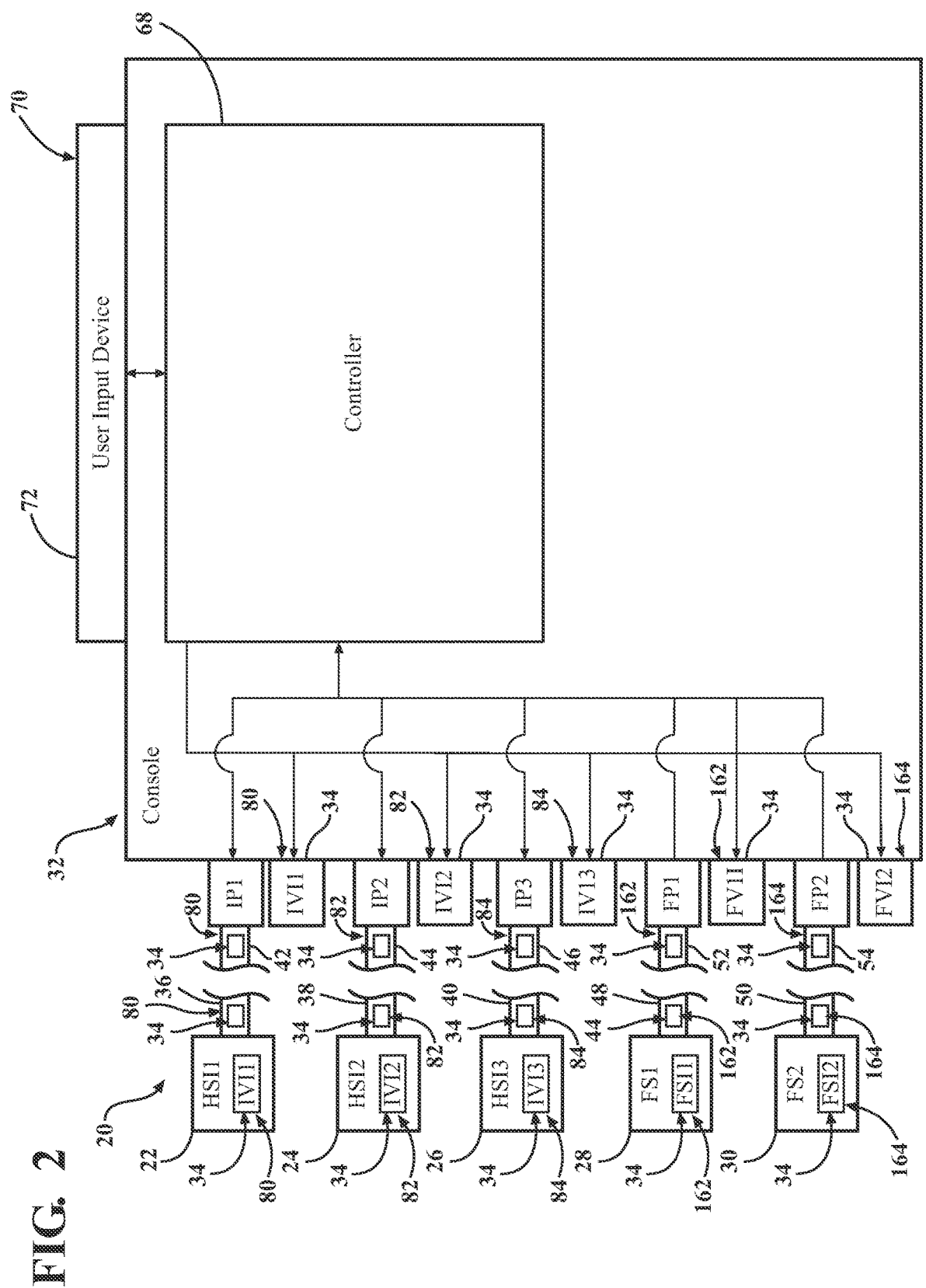
FIG. 2 is a schematic view of the console-based surgical system of FIG. 1, the system includes a first handheld surgical instrument, a second handheld surgical instrument, a third handheld surgical instrument, a first footswitch, and a second footswitch.

Referring to FIG. 2, the console 32 further comprises a controller 68 configured to associate one of the first, second, and third instrument ports 56, 58, 60 with the first footswitch port 64, such that the first footswitch 28 is operable to actuate a function of the handheld surgical instruments connected to the associated instrument port. Similarly, the controller 68 is configured to associate another one of the first, second, and third instrument ports 56, 58, 60, with the second footswitch port 66 such that the second footswitch 30 is operable to actuate a function of the handheld surgical instrument connected with the associated instrument port. It is contemplated that the controller 68 may associate the same instrument port with both of the first and second footswitch ports 64, 66, such that the footswitches 28, 30 are operable to actuate a function of the same handheld surgical instrument connected to the associated instrument port. The association of instrument ports with footswitch ports is addressed in detail in the description for FIGS. 6-17. The console 32 is capable of being coupled to a power source (not shown) to receive power therefrom and deliver the same to any one or more of the instruments 22, 24, 26, and the footswitches 28, 30. In other embodiments, the connector lines for the handheld surgical instruments and/or footswitches may be omitted and the console may be connected wirelessly therewith.

The system 20 may further comprise a user input device 70 coupled to the controller 68 and actuatable by a user to output one or more user output signals to cause the controller 68 to associate one of the instrument ports 56, 58, 60 with one of the footswitches 28, 30. In one embodiment, the user input device 70 can be a touchscreen panel 72 or any other user input device configured to permit a surgeon to indicate which footswitch assignments are wanted for the present operation. More specifically, the controller 68 may comprise a circuit (not shown) that, based on instructions from the touchscreen panel 72 or other user input device, generates energization signals transmitted to the motors (not shown) or other power-consuming units (not shown) internal to the instrument(s) coupled to the associated instrument port(s). The controller 68 can be simultaneously connected to the first, second, and third handheld surgical instruments 22, 24, 26 through the corresponding plugs 42, 44, 46 and connector lines 36, 38, 40. The controller 68 may provide data and receive instructions from the user input device 70 over a second SPI bus (not shown).

Referring to FIG. 3, in this embodiment, the touchscreen panel 72 may comprise a plurality of icons 74, 76, 78 for the first, second, and third instrument ports 56, 58, 60 that are to be associated, assigned, or mapped to one or both of the footswitch ports 64, 66. Upon the surgeon touching the icon for each instrument port, the controller 68 may change the footswitch mapping for that instrument port. Specifically, the controller 68 cycles the mapping for each instrument port through the following sequence: the first footswitch port 64; the second footswitch port 66; dual control mode for both the first and second footswitch ports 64, 66; and no footswitch control. As the mapping changes, the color of the icon changes appropriately to indicate the new assignment for the associated instrument. Acceptance of a specific footswitch assembly assignment map is performed by depressing an icon (not shown) for an accept (ACPT) button also presented on the user input device 70. Other embodiments without the accept button are contemplated, such that the icons 74, 76, 78 are toggle buttons that require no confirmation of the selected mapping.

In response to the surgeon depressing one or more of the icons 74, 76, 78 to select a footswitch assembly assignment association, the controller 68 records the new footswitch association into footswitch association tables (not shown). The surgeon(s) may then able to use or actuate each instrument by depressing the appropriate pedal on the footswitch assigned to control the associated instrument.

Also in this embodiment, the footswitch assignment association can only be performed by depressing the icons 74, 76, 78 presented on the touchscreen panel 72. This prevents inadvertent depression of the footswitches for unintentionally transferring control of an instrument from one of the two footswitches 28, 30 to the other of the two footswitches 28, 30. However, it is contemplated that other embodiments of the system may include switches (not shown) for separating control of an instrument from a footswitch or transferring control from one footswitch to another, with those switches attached to the footswitches, instruments, connector lines, or any portion of the system. As one example, the surgeon may choose to actuate an instrument-mounted switch to regulate the actuation of the instrument. When this option is selected, the associated icon on the user input device 70 is presented as a grey, and none of the footswitches are operable to control the handheld surgical instrument.

Furthermore, the system 20 may be disposed in a "plug and play" mode for one footswitch, such that the controller 68 assigns instrument ports to footswitch ports according to a default scheme. Independent or in the absence of a user output signal from the user input device 70, the controller 68 can be configured to automatically associate one of the instrument ports 56, 58, 60 with one or more of the footswitch ports 64, 66. More specifically, under this default scheme, if there is just a single footswitch operably connected to either the first footswitch port 64 or the second footswitch port 66, each one of the first, second, and third instrument ports 56, 58, 60 is associated, assigned, or mapped to that connected footswitch port, such that the footswitch controls each one of the first, second, and third instruments 22, 24, 26.

Similarly, the system 20 may be further disposed in the "plug and play" mode for one instrument when the connector lines 48, 50 of the first and second footswitches 28, 30 are coupled to the first and second footswitch ports 64, 66 and the connector line of only one instrument is coupled to one of the first, second, or third instrument ports 56, 58, 60. The controller 68 performs default mapping for this version of the "plug and play" mode by mapping control for the instrument to each one of the first and second footswitches 28, 30. When both footswitches 28, 30 can control an instrument, the instrument is considered to be in a "dual-control" mode.

If the controller 68 determines that two or more instruments and the first and second footswitches 28, 30 are connected to the console 32, the system 20 is disposed in a "multiple" mode. Initially, when the system 20 enters the "multiple" mode, the controller 68 maps the footswitch assignments to what they were in the immediate past "plug and play" mode. Thus, if a single footswitch was controlling the plurality of instruments, that footswitch retains control of those instruments. Conversely, if both footswitches 28, 30 had a single instrument under dual control, both footswitches 28, 30 maintain this control.

The visual indicators 34 may comprise a plurality of instrument visual indicators 80, 82, 84 coupled to the corresponding instruments 22, 24, 26, connector lines 36, 38, 40 for the same, and/or portions of the console 32 adjacent to the first, second, and third instrument ports 56, 58, 60. The visual indicators 34 may further include a plurality of footswitch visual indicators 162, 164 coupled to the corresponding footswitches 28, 30, connector lines 48, 50, for the same, and/or portions of the console 32 adjacent to the first and second footswitch ports 64, 66. It is contemplated that the visual indicators may be coupled to any one or more of the instruments, footswitches, connector lines, or console (either the display, instrument ports, or footswitch ports) and may take a variety of forms, including but not limited to, light emitters, displays, electromechanical devices, etc. For example, if the visual indicator takes the form of the touchscreen panel or display, the display can show the icons 74, 76, 78, symbol, illustration, or verbal description of the type of association. Other embodiments of the visual indicators can comprise any suitable light emitter or mechanically-operated posts, flags, buttons, or other visual indicators.

Figure 4:
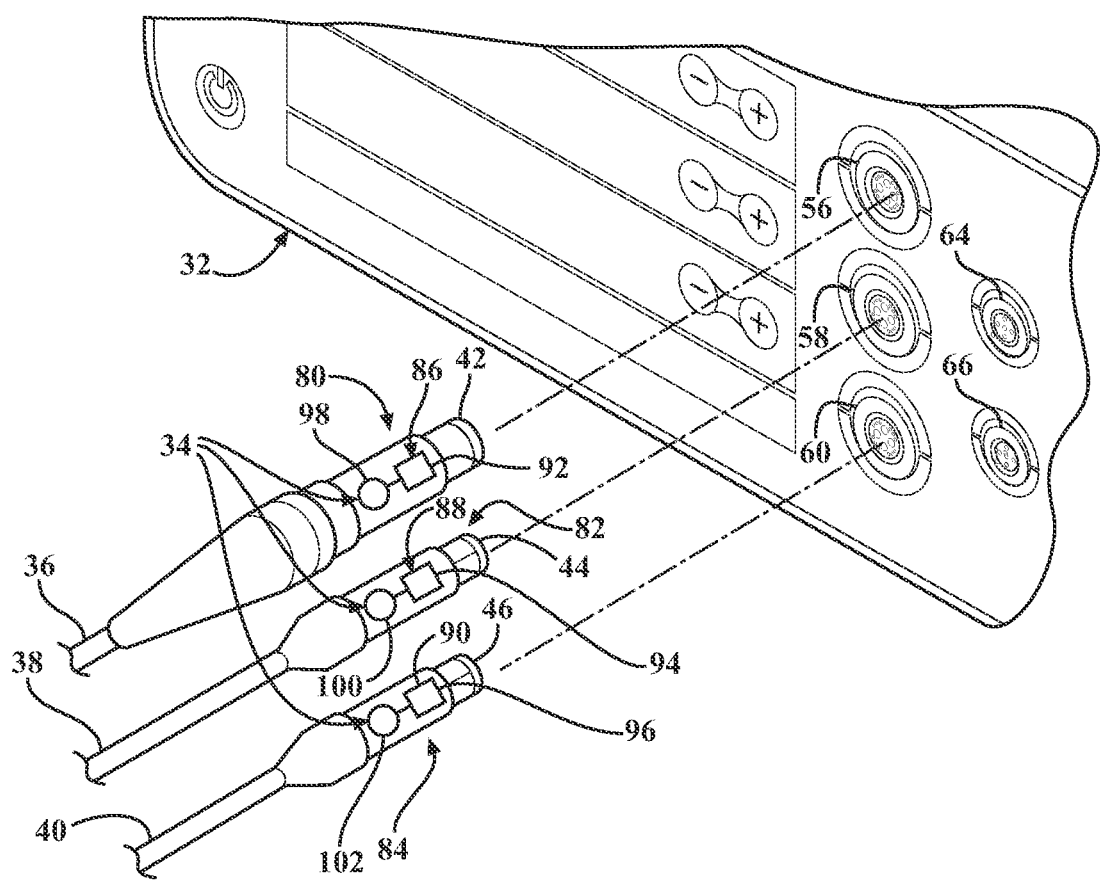
FIG. 4 is an enlarged view of illustrating first, second, and third instrument plugs capable of being connected to the first, second, and third instrument ports of the console shown in FIG. 1, with the first, second, and third instrument plugs comprising first, second, and third instrument visual indicators.

Referring to FIG. 4, one portion of the instrument visual indicators 80, 82, 84 may be coupled to the plugs 42, 44, 46 of the connector lines 36, 38, 40. Each one of these instrument visual indicators 80, 82, 84 on the plugs 42, 44, 46 may comprise a light emitter 86, 88, 90. More specifically, the light emitters 86, 88, 90 may comprise one or more LEDs 92, 94, 96, ring-shaped light guides 98, 100, 102, or combinations thereof. In this embodiment, each one of the LEDs 92, 94, 96 comprises a multi-colored light emitter configured to emit a plurality of colored lights. However, the instrument visual indicators 80, 82, 84 on the plugs 42, 44, 46 may take a variety of forms, including but not limited to, light emitters, fiber optic strips, displays, electromechanical devices, etc. It is contemplated that the instrument visual indicators on the plugs 42, 44, 46 can comprise any suitable light emitter or mechanically-operated posts, flags, buttons, or other visual indicators. Other embodiments comprising any number or type of visual indicators coupled to any portion(s) of the plugs 42, 44, 46 are contemplated. In addition, embodiments of any one or more of the plugs 42, 44, 46 without instrument visual indicators are also contemplated.

Figure 5:
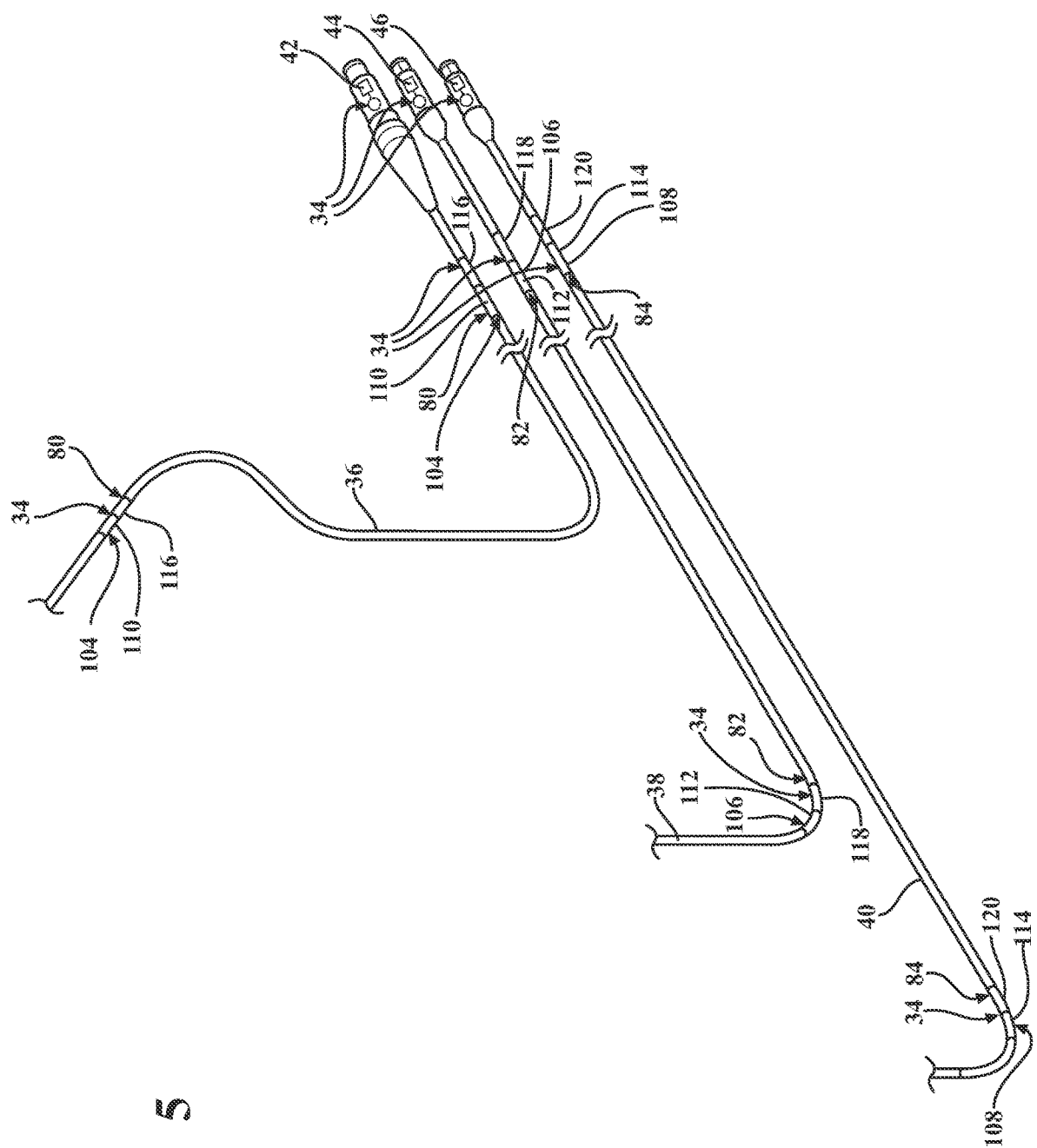
FIG. 5 is an enlarged view of first, second, and third connector lines for the first, second, and third handheld surgical instruments shown in FIG. 1, with the first, second, and third connector lines comprising first, second, and third instrument visual indicators.

Referring to FIG. 5, another portion of instrument visual indicators 80, 82, 84 may be integrated or embedded within one or both ends of each connector lines 36, 38, 40. In the illustrated embodiment, each end of the connector lines 36, 38, 40 comprises a light emitter 104, 106, 108. More specifically, the light emitters 104, 106, 108 may comprise one or more LEDs 110, 112, 114, fiber optic or light strips 116, 118, 120, or combinations thereof. In this embodiment, each one of the LEDs 110, 112, 114 comprises a multi-colored light emitter configured to emit a plurality of colored lights. However, the instrument visual indicators 80, 82, 84 on one or both ends of the connector lines 36, 38, 40 may take a variety of forms, including but not limited to, light emitters, ring-shaped light guides, displays, electromechanical devices, etc. It is contemplated that the instrument visual indicators on the connector lines 36, 38, 40 can comprise any suitable light emitter or mechanically-operated posts, flags, buttons, or other visual indicators. Other embodiments of the instrument visual indicators 80, 82, 84 are coupled to intermediate portions of the corresponding connector lines 36, 38, 40 between the opposing ends of those connector lines 36, 38, 40. Still other embodiments of the instrument visual indicators 80, 82, 84 may comprise a single visual indicator coupled to each corresponding connector line 36, 38, 40 and extending along the entire length, or a portion thereof. Other embodiments comprising any number or type of visual indicators coupled to any portion(s) of the connector lines 36, 38, 40 are contemplated. In addition, embodiments of any one or more of the connector lines 36, 38, 40 without any instrument visual indicators are also contemplated.

Figure 6:
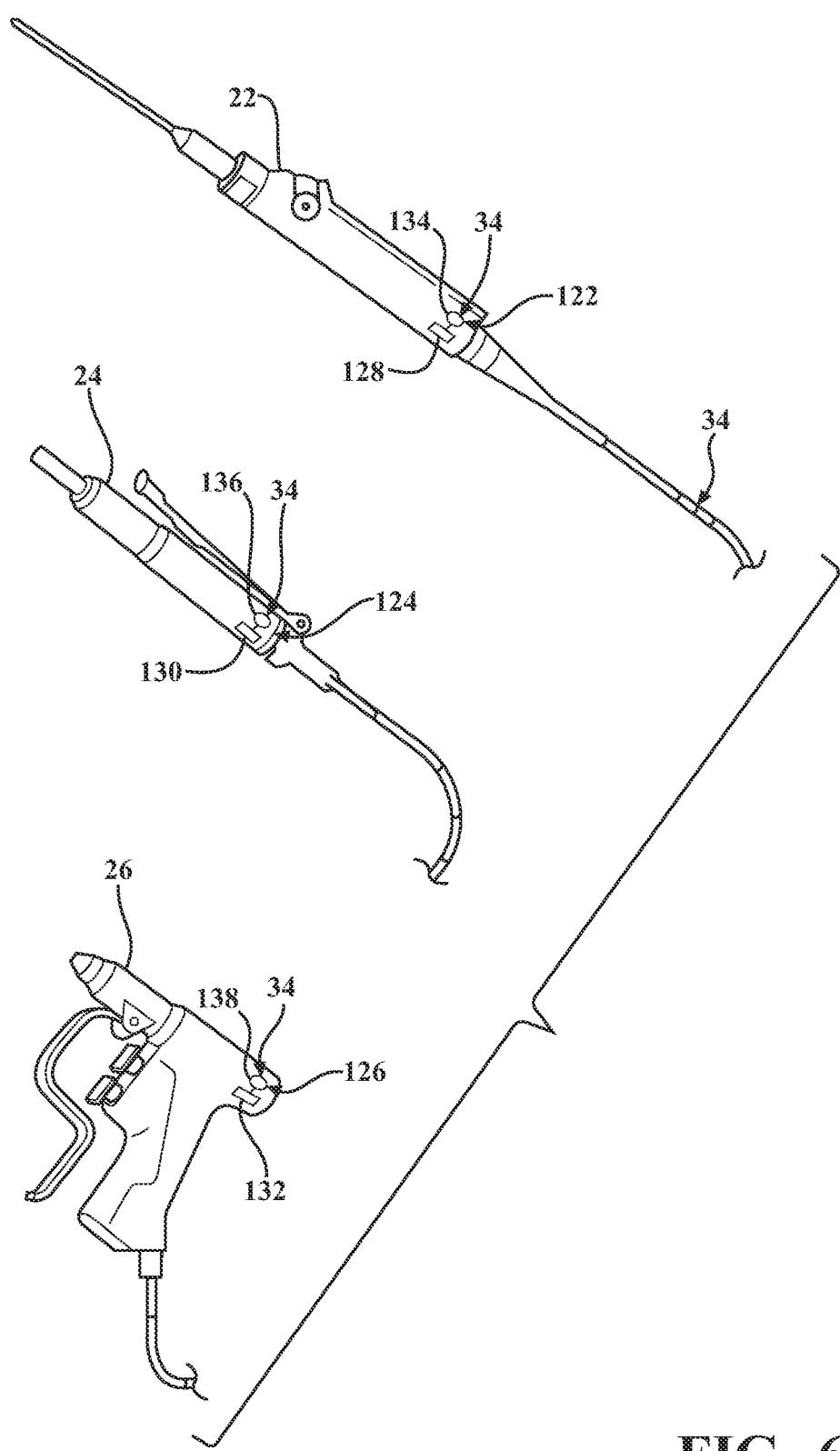
FIG. 6 is an enlarged view of the first, second, and third instruments shown in FIG. 1, illustrating the first, second, and third instruments comprising first, second, and third instrument visual indicators.

Referring to FIG. 6, still another portion of instrument visual indicators 80, 82, 84 may be integrated or embedded within one or more of the first, second, or third handheld surgical instruments 22, 24, 26. In the illustrated embodiment, each instrument visual indicator 80, 82, 84 may comprise a light emitter 122, 124, 126 in the form of LEDs 128, 130, 132, ring-shaped light guides 134, 136, 138, or combinations thereof. In this embodiment, each one of the LEDs 128, 130, 132 comprises a multi-colored light emitter configured to emit a plurality of colored lights. However, the instrument visual indicators 80, 82, 84 on one or more of the instruments 22, 24, 26 may take a variety of forms, including but not limited to, light emitters, fiber optic strips, displays, electromechanical devices, etc. For instance, if the instrument visual indicator takes the form of the touchscreen panel or display, the display can show an icon, symbol, illustration, or verbal description of the type of association. It is contemplated that the instrument visual indicators on the instruments 22, 24, 26 can comprise any suitable light emitter or mechanically-operated posts, flags, buttons, or other visual indicators. Other embodiments of the instrument visual indicators 80, 82, 84 may comprise any number or type of visual indicators coupled to any portion(s) of the instruments 22, 24, 26. In addition, embodiments of any one or more of the instruments 22, 24, 26 without any instrument visual indicators are also contemplated.

Figure 7:
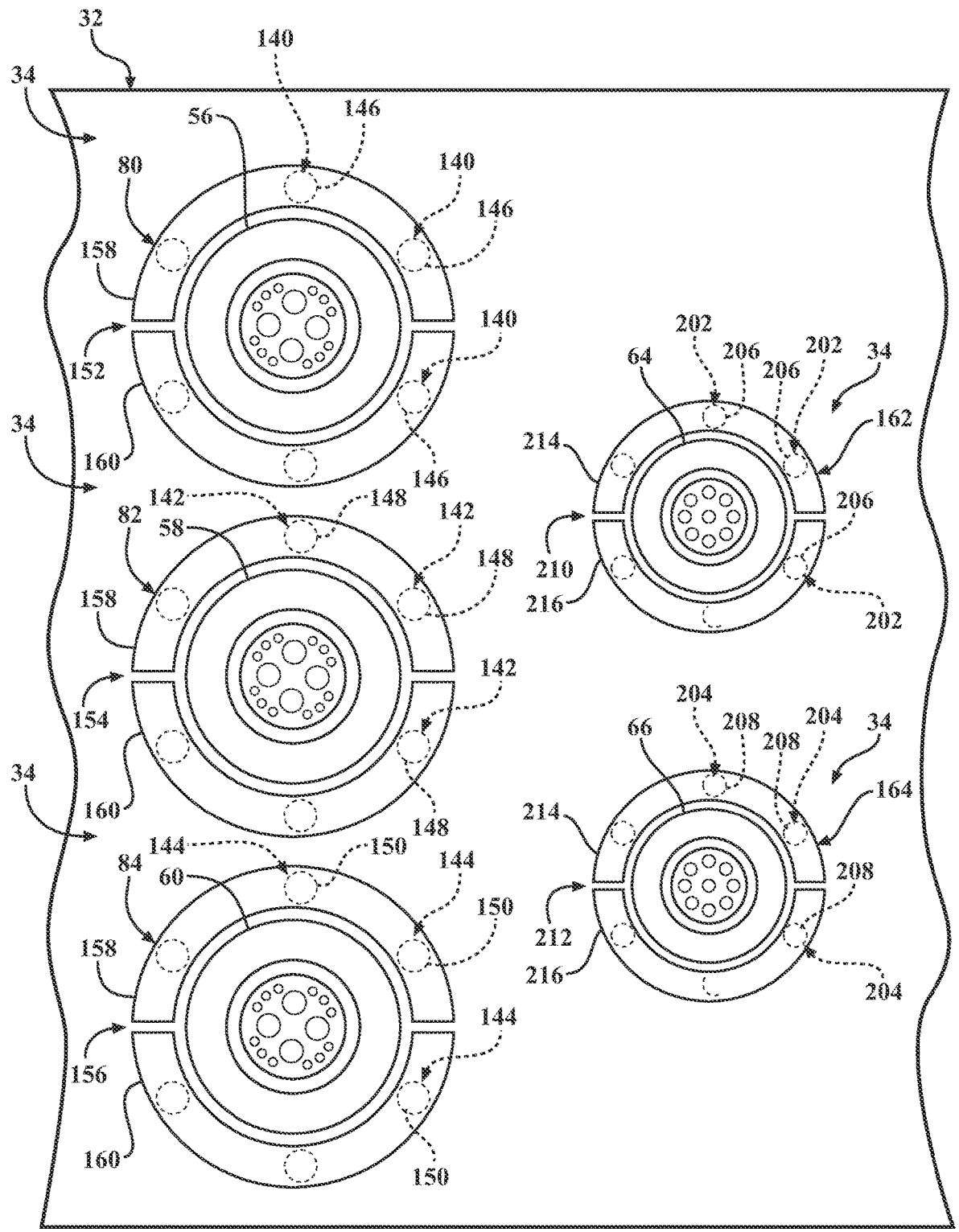
FIG. 7 is an enlarged view of the first, second, and third instrument ports and first and second footswitch ports of the console shown in FIG. 3, illustrating first, second, and third instrument visual indicators and first and second footswitch visual indicators coupled to the console.

Referring to FIG. 7, a portion of instrument visual indicators 80, 82, 84 may be integrated or coupled to the console 32 adjacent to a corresponding one of the first, second, and third instrument ports 56, 58, 60. In the illustrated embodiment, each instrument visual indicator 80, 82, 84 may comprise the light emitter 140, 142, 144 in the form of LEDs 146, 148, 150, ring-shaped light guides 152, 154, 156, or combinations thereof. Each ring-shaped light guide 152, 154, 156 may be coupled to the console 32 and surround a corresponding one of the first, second, and third instrument ports 56, 58, 60. Each ring-shaped light guide 152, 154, 156 can comprise two arcuate light emitter portions 158, 160 on opposing sides of the corresponding port, with one light emitter portion 158 adjacent to the other light emitter portion 160. While FIG. 1 illustrates the light emitter portion 158 positioned above the light emitter portion 160 in a vertical arrangement, it is contemplated that the light emitter portions 158, 160 can be positioned lateral to one another in a side-by-side arrangement or in any other suitable arrangement. In this embodiment, each one of the light emitter portions 158, 160 comprises a multi-colored light emitter configured to emit a plurality of colored lights. However, the instrument visual indicators 80, 82, 84 on the console 32 may take a variety of forms, including but not limited to, light emitters, fiber optic strips, displays, electromechanical devices, etc. For instance, if the instrument visual indicator takes the form of the touchscreen panel or display, the display can show an icon 74, 76, 78, symbol, illustration, or verbal description of the type of association. It is contemplated that the instrument visual indicators on the console 32 can comprise any suitable light emitter or mechanically-operated posts, flags, buttons, or other visual indicators. Other embodiments of the instrument visual indicators 80, 82, 84 may be coupled to a top side, a left side, a right side, a bottom side, a rear side, other portions of the front side, any portion of the console, or combinations thereof. Other embodiments comprising any number or type of visual indicators are contemplated. In addition, embodiments of the console 32 without any instrument visual indicators are also contemplated.

Referring to FIG. 8, footswitch visual indicators 162, 164 may be coupled to the first and second plugs 52, 54 of the first and second connector lines 48, 50. Each one of these footswitch visual indicators 162, 164 on the first and second plugs 52, 54 comprises a light emitter 170, 172. More specifically, the light emitters 170, 172 may comprise one or more LEDs 174, 176, ring-shaped light guides 177, 179, or combinations thereof. In this embodiment, each one of the LEDs 174, 176 comprises a multi-colored light emitter configured to emit a plurality of colored lights. However, the footswitch visual indicators 162, 164 on the plugs 52, 54 may take a variety of forms, including but not limited to, light emitters, fiber optic strips, displays, electromechanical devices, etc. It is contemplated that the footswitch visual indicators on the plugs 52, 54 can comprise any suitable light emitter or mechanically-operated posts, flags, buttons, or other visual indicators. Other embodiments comprising any number or type of visual indicators coupled to any portion(s) of the plugs 52, 54 are contemplated. In addition, embodiments of any one or more of the plugs 52, 54 without footswitch visual indicators are also contemplated.

Referring to FIG. 9, another portion of footswitch visual indicators 162, 164 may be integrated or embedded within one or both ends of each connector lines 48, 50. In the illustrated embodiment, each end of the connector lines 48, 50 comprises a light emitter 178, 180. More specifically, the light emitters 178, 180 may comprise one or more LEDs 182, 184, fiber optic strips 186, 188, or combinations thereof. In this embodiment, each one of the LEDs 182, 184 comprises a multi-colored light emitter configured to emit a plurality of colored lights. However, the footswitch visual indicators 162, 164 on one or both ends of the connector lines 48, 50 may take a variety of forms, including but not limited to, light emitters, ring-shaped light guides, displays, electromechanical devices, etc. It is contemplated that the footswitch visual indicators on the connector lines 48, 50 can comprise any suitable light emitter or mechanically-operated posts, flags, buttons, or other visual indicators. Other embodiments of the footswitch visual indicators 162, 164 are coupled to intermediate portions of the corresponding connector lines 48, 50 between the opposing ends of those connector lines 48, 50. Still other embodiments of the footswitch visual indicators 162, 164 may comprise one or more visual indicators coupled to each corresponding connector line 48, 50, such as light strips extending along the entire length, or a portion thereof. Other embodiments comprising any number or type of visual indicators coupled to any portion(s) of the connector lines 48, 50 are contemplated. In addition, embodiments of any one or more of the connector lines 48, 50 without any footswitch visual indicators are also contemplated.

Referring to FIG. 10, still another portion of footswitch visual indicators 162, 164 may be integrated or embedded within one or more of the first or second footswitches 28, 30. In the illustrated embodiment, each footswitch visual indicator 162, 164 comprises a light emitter 190, 192. More specifically, the light emitters 190, 192 may comprise one or more LEDs 194, 196, ring-shaped light guides 198, 200 or combinations thereof. In this embodiment, each one of the LEDs 194, 196 comprises a multi-colored light emitter configured to emit a plurality of colored lights. However, the footswitch visual indicators 162, 164 on one or more of the footswitches 28, 30 may take a variety of forms, including but not limited to, light emitters, fiber optic strips, displays, electromechanical devices, etc. For instance, if the footswitch visual indicator takes the form of the touchscreen panel or display, the display can show an icon, symbol, illustration, or verbal description of the type of association. It is contemplated that the footswitch visual indicators on the footswitches 28, 30 can comprise any suitable light emitter or mechanically-operated posts, flags, buttons, or other visual indicators. Other embodiments of the footswitch visual indicators 162, 164 may comprise any number or type of visual indicators coupled to any portion(s) of the footswitches 28, 30. In addition, embodiments of any one or more of the footswitches 28, 30 without any footswitch visual indicators are also contemplated.

Referring back to FIG. 7, footswitch visual indicators 162, 164 may be integrated or coupled to the console 32 adjacent to a corresponding one of the first and second footswitch ports 64, 66. In the illustrated embodiment, each footswitch visual indicator 162, 164 may comprise a light emitter 202, 204. The light emitters 202, 204 may comprise series of LEDs 206, 208, ring-shaped light guides 210, 212, or combinations thereof. Each ring-shaped light guide 210, 212 may be coupled to the console 32 and surround a corresponding one of the footswitch ports 64, 66. Each ring-shaped light guide 210, 212 can comprise two arcuate light emitter portions 214, 216 on opposing sides of the corresponding port, with one light emitter portion 214 adjacent to the other light emitter portion 216. While FIG. 1 illustrates the light emitter portion 214 positioned above the light emitter portion 216 in a vertical arrangement, it is contemplated that the light emitter portions 214, 216 can be positioned lateral to one another in a side-by-side arrangement or in any other suitable arrangement. In this embodiment, each one of the light emitter portions 214, 216 comprises a multi-colored light emitter configured to emit a plurality of colored lights. However, the footswitch visual indicators 162, 164 on the console 32 may take a variety of forms, including but not limited to, light emitters, fiber optic strips, displays, electromechanical devices, etc. For instance, if the footswitch visual indicator takes the form of the touchscreen panel or display, the display can show the icons 74, 76, 78 (FIG. 3), symbol, illustration, or verbal description of the type of association. It is contemplated that the footswitch visual indicators on the console can comprise any suitable light emitter or mechanically-operated posts, flags, buttons, or other visual indicators. Other embodiments of the footswitch visual indicators 162, 164 may be coupled to a top side, a left side, a right side, a bottom side, a rear side, other portions of the front side, any portion of the console, or combinations thereof. Other embodiments comprising any number or type of visual indicators are contemplated. In addition, embodiments of the console 32 without any footswitch visual indicators are also contemplated.

Figure 11:
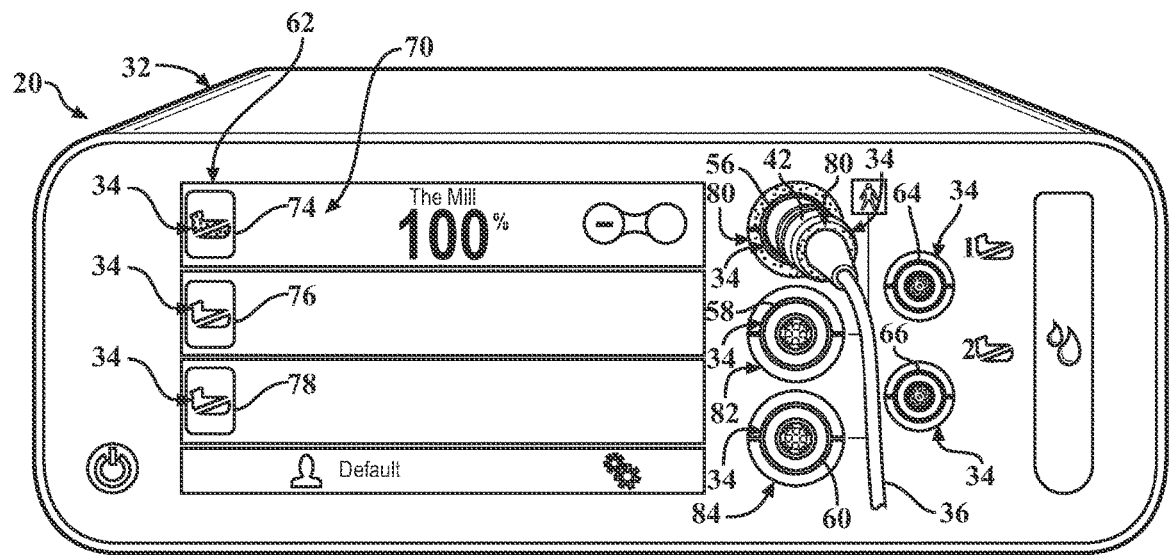
FIG. 11 is a front perspective view of the console of FIG. 3, illustrating the first connector line of the first handheld surgical instrument coupled to the first instrument port.
Figure 12:
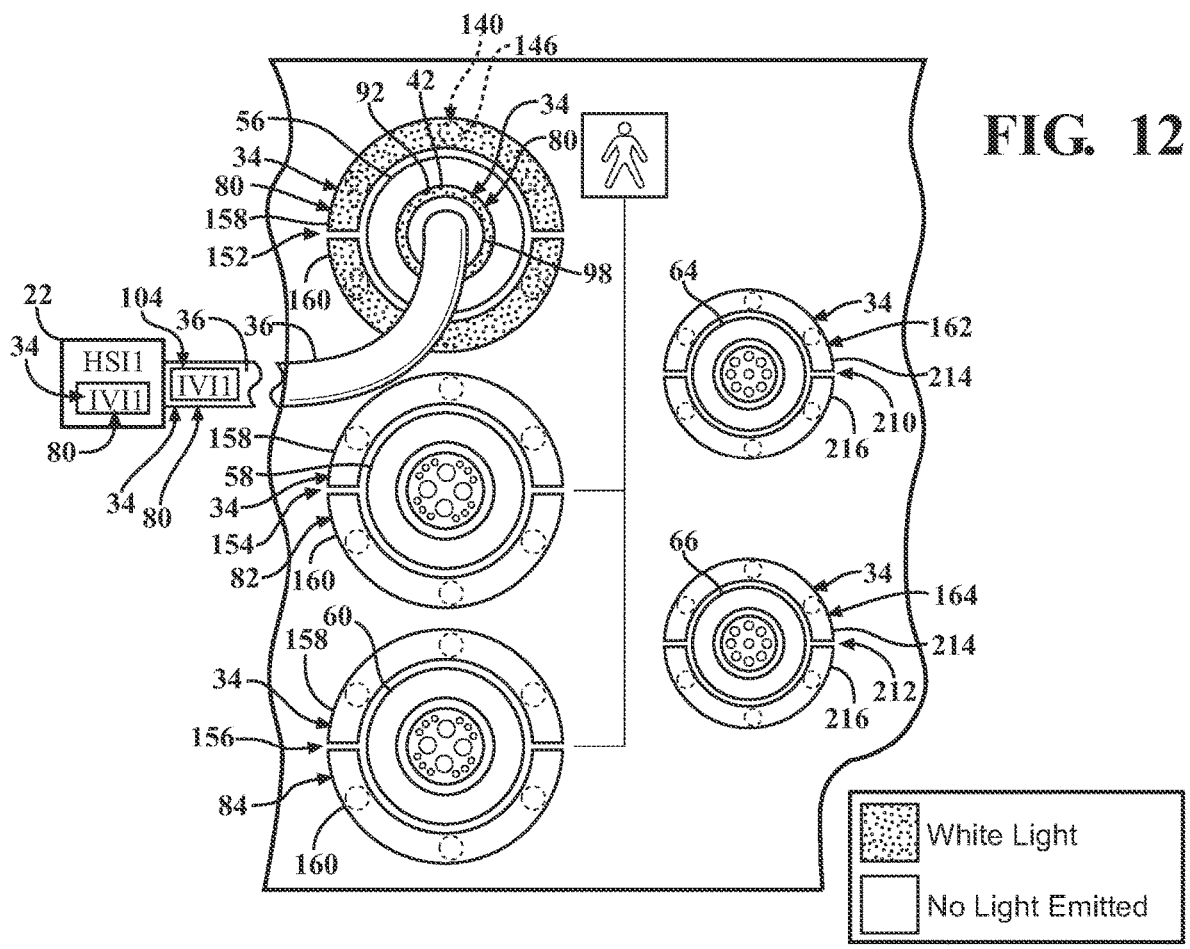
FIG. 12 is an enlarged view of the instrument ports and footswitch ports of FIG. 11, illustrating first instrument visual indicators coupled to the first surgical handheld instrument, the connector line for the first surgical handheld instrument, and the console adjacent to the first instrument port to indicate that the first instrument port is not associated with any of the footswitch ports.

Referring now to FIGS. 11 and 12, there is illustrated the system 20 of FIG. 3 comprising the first connector line 36 of the first instrument coupled to the first instrument port 56. In the illustrated embodiment, the system 20 does not comprise the connector line of any footswitch or other input device being connected to either one of the footswitch ports 64, 66. Furthermore, the controller 68 has not associated the first instrument port 56 with either one of the unoccupied footswitch ports 64, 66. The controller 68 activates the first instrument visual indicators 80 of the first instrument port 56, the first plug 42, the connector line 36, the first instrument 22, and any combinations thereof to indicate that the first instrument port 56 is not associated with either one of the footswitch ports 64, 66.

More specifically, in the illustrated embodiment, the instrument visual indicator 80 on the console 32 may comprise the light emitter 140 in the form of the LEDs 146 and the ring-shaped light guide 152 coupled to the console 32 and surrounding the first instrument port 56. The ring-shaped light guide 152 may comprise the two arcuate light emitter portions 158, 160 on opposing sides of the first instrument port 56, with one light emitter portion 158 adjacent to the other light emitter portion 160. The controller 68 activates the LEDs 146 to emit white light through the light emitter portions 158, 160 to indicate that the first instrument port 56 is not associated with either one of the footswitch ports 64, 66. However, the instrument visual indicator 80 on the console 32 may emit any colored light and take a variety of forms, including but not limited to, light emitters, fiber optic strips, displays, electromechanical devices, etc. to indicate that the first instrument port 56 is not associated with either one of the footswitch ports 56, 58. For instance, if the instrument visual indicator takes the form of the touchscreen panel or display, the display can show an icon 74, symbol, illustration, or verbal description of the type of association. It is contemplated that the instrument visual indicators can comprise any suitable light emitter or mechanically-operated posts, flags, buttons, or other visual indicators. Other embodiments of the instrument visual indicator may be coupled to a top side, a left side, a right side, a bottom side, a rear side, other portions of the front side, any portion of the console, or combinations thereof. Still other embodiments comprising any number or type of visual indicators are contemplated. In addition, embodiments of the console 32 not comprising any instrument visual indicators are also contemplated.

The instrument visual indicator 80 coupled to the plug 42 may comprise the light emitter 86 of FIG. 4 in the form of the LEDs 92 and ring-shaped light guide 98. In this embodiment, the LED 92 comprises the multi-colored light emitter configured to emit a plurality of colored lights. However, the instrument visual indicator 80 on the plug 42 may take a variety of forms, including but not limited to, light emitters, fiber optic strips, displays, electromechanical devices, etc. It is contemplated that the instrument visual indicators on the plug 42 can comprise any suitable light emitter or mechanically-operated posts, flags, buttons, or other visual indicators. Other embodiments comprising any number or type of visual indicators coupled to any portion(s) of the plug 42 are contemplated. In addition, other embodiments of the plug 42 without the instrument visual indicator are also contemplated.

The instrument visual indicator 80 integrated or embedded within the connector line 36 may comprise the light emitter 104 of FIG. 5 in the form of the LED 110 and/or fiber optic/light strip(s) 116. In the illustrated embodiment, the LED comprises the multi-colored light emitter configured to emit a plurality of colored lights. However, the instrument visual indicator 80 on one or both ends of the connector line 36 may take a variety of forms, including but not limited to, light emitters, ring-shaped light guides, displays, electromechanical devices, etc. It is contemplated that the instrument visual indicators on the connector line 36 may comprise any suitable light emitter or mechanically-operated posts, flags, buttons, or other visual indicators. Other embodiments of the instrument visual indicator 80 are coupled to intermediate portions of the connector line 36 between the opposing ends of the connector line 36. Still other embodiments of the instrument visual indicator 80 may comprise a single visual indicator coupled to the connector line 36 and extending along the entire length thereof. Other embodiments comprising any number or type of visual indicators coupled to any portion(s) of the connector lines 36 are contemplated. In addition, embodiments of the connector line 36 without any instrument visual indicators are also contemplated.

The instrument visual indicator 80 integrated or embedded within the first handheld surgical instrument 22 may comprise the light emitter 122 of FIG. 6 in the form of the 128 LED and ring-shaped light guide 134. In the illustrated embodiment, the LED 128 may comprise a multi-colored light emitter configured to emit a plurality of colored lights. However, the instrument visual indicator on the first handheld surgical instrument 22 may take a variety of forms, including but not limited to, light emitters, fiber optic strips, displays, electromechanical devices, etc. For instance, if the instrument visual indicator takes the form of the touchscreen panel or display, the display can show an icon, symbol, illustration, or verbal description of the type of association. It is contemplated that the instrument visual indicators on the instruments 22 can comprise any suitable light emitter or mechanically-operated posts, flags, buttons, or other visual indicators. Other embodiments of the instrument visual indicator 80 may comprise any number or type of visual indicators coupled to any portion(s) of the instruments 22. In addition, other embodiments of the instrument 22 without any instrument visual indicators are also contemplated.

Referring generally to FIGS. 13-24, the controller is further configured to activate the footswitch visual indicators and the instrument visual indicators of the associated instrument port to display outputs that correspond with one another. More specifically, in the illustrated embodiments, the controller is further configured to activate the footswitch visual indicators 162, 164 on the footswitches 28, 30, connector lines 48, 50, plugs 52, 54, and footswitch ports 64, 66 and the instrument visual indicators 80, 82, 84 on the instruments 22, 24, 26, connector lines 36, 38, 40, plugs 42, 44, 46, and instrument ports 56, 58, 60 to display outputs that correspond with one another. In these embodiments, the footswitch visual indicators 162, 164 and the instrument visual indicators 80, 82, 84 are respective ones of the light emitters 104, 106, 86, 88, 90 of FIG. 7, which display outputs that correspond with one another by emitting colored light that matches one another. It should be appreciated that the displaying outputs that correspond with one another should be broadly understood to mean that users seeing the outputs of the footswitch visual indicators and the instrument visual indicators would understand that there is a relation therebetween. As such, aside from matching of colors, correspondence should be understood to mean any pattern, text, symbol, or other visual-detectable element that would be understood to reveal an association between the two or more visual indicators.

Figure 13:
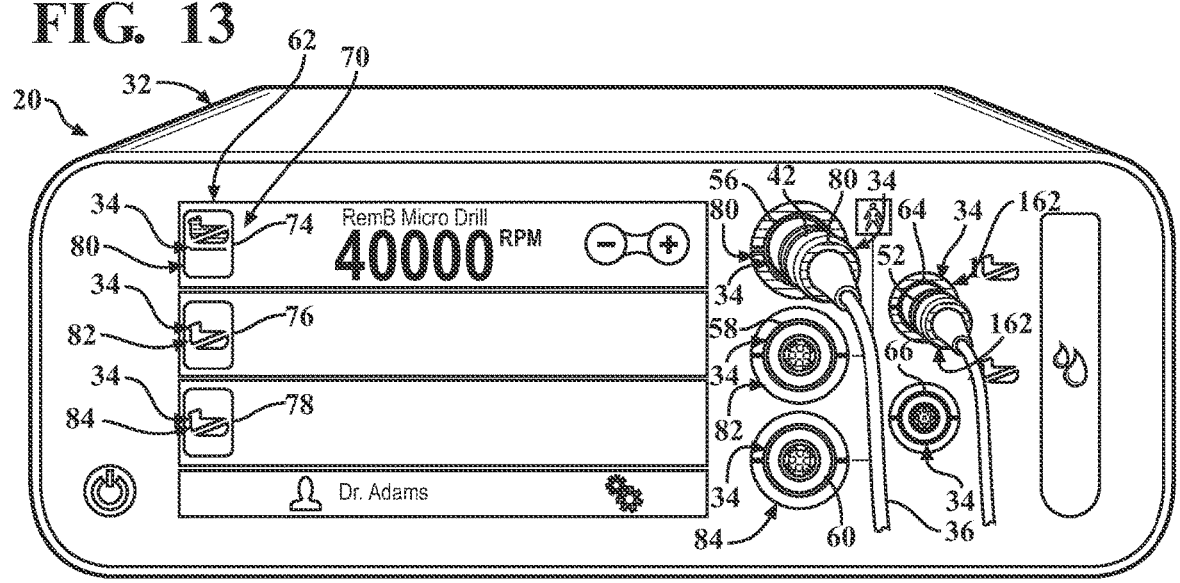
FIG. 13 is a front perspective view of the console of FIG. 3, illustrating the first connector line of the first handheld surgical instrument coupled to the first instrument port and the first connector line of the first footswitch coupled to the first footswitch port.
Figure 14:
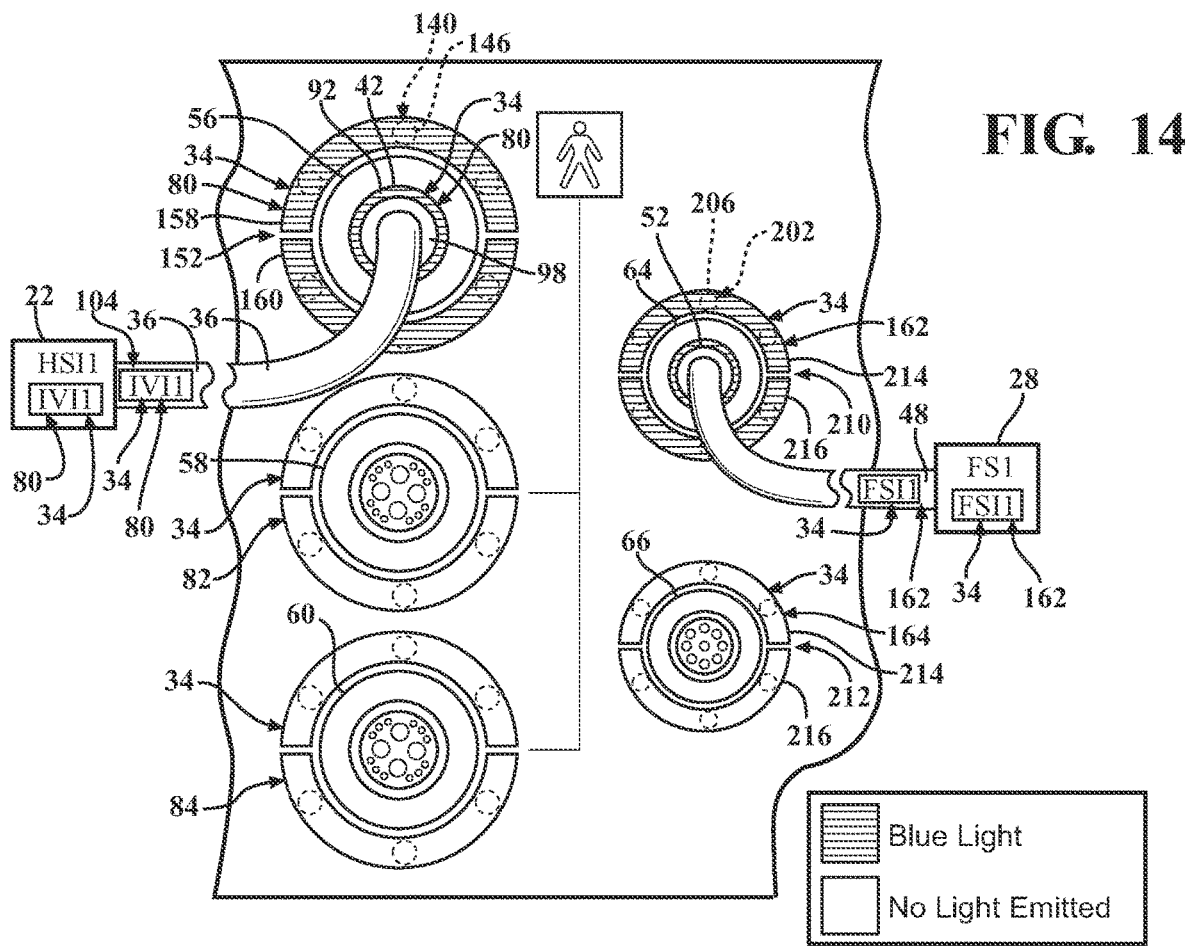
FIG. 14 is an enlarged view of the instrument ports and footswitch ports of FIG. 13, with an association between the first instrument port and the first footswitch port being indicated by first instrument visual indicators and first footswitch visual indicators coupled to the console.

More specifically, in FIGS. 13 and 14, the controller associates the first instrument port 56 with the first footswitch port 64, and the controller activates one or more of instrument visual indicators 80 of the associated first instrument port 56 and one or more of the footswitch visual indicators 162 of the first footswitch port 64 to display outputs corresponding with one another. In the illustrated embodiment, the controller activates the instrument visual indicators 80 of the associated first instrument port 56 and the footswitch visual indicators 162 of the first footswitch port 64 to emit colors that match one another.

The instrument visual indicator 80 of the associated first instrument port 56 on the console 32 may comprise the light emitter as shown in FIG. 7 in the form of the LEDs 146 and ring-shaped light guide 152. The ring-shaped light guide 152 may be coupled to the console 32 and surround the first instrument port 56. The ring-shaped light guide 152 may comprise two arcuate light emitter portions 158, 160 on opposing sides of the first instrument port 56, with one light emitter portion 158 adjacent to the other light emitter portion 160. While FIG. 14 illustrates the light emitter portion 158 positioned above the light emitter portion 160 in a vertical arrangement, it is contemplated that the light emitter portions 158, 160 can be positioned lateral to one another in a side-by-side arrangement or in any other suitable arrangement. In this embodiment, each one of the LEDs 146 comprises a multi-colored light emitter configured to emit a plurality of colored lights. The controller 68 may activate the LEDs 146 to emit a colored light through both light emitter portions 158, 160 that matches a colored light emitted by any one or more of the footswitch visual indicators 162 on the console 32, the plug 52, the connector line 48, and the footswitch 28. In the illustrated embodiment, the controller 68 activates the LEDs 146 to emit a blue light through both light emitter portions 158, 160 to match the blue light emitted by the footswitch visual indicators 162 on each one of the console 32, the plug 52, the connector line 48, and the footswitch 28.

The footswitch visual indicator 162 of the first footswitch port 64 on the console 32 may comprise a light emitter 202 as shown in FIG. 7 in the form of the LEDs 206 and ring-shaped light guide 210. The ring-shaped light guide 210 may be coupled to the console 32 and surround the first footswitch port 64. The ring-shaped light guide 210 can comprise two arcuate light emitter portions 214, 216 on opposing sides of the first footswitch port 64, with one light emitter portion 214 adjacent to the other light emitter portion 216. While FIG. 14 illustrates the light emitter portion 214 positioned above the light emitter portion 216 in a vertical arrangement, it is contemplated that the light emitter portions 214, 216 can be positioned lateral to one another in a side-by-side arrangement or in any other suitable arrangement. In this embodiment, each one of the LEDs 206 comprises a multi-colored light emitter configured to emit a plurality of colored lights. The controller may activate the LEDs 206 to emit a colored light that matches the colored light emitted by any one or more of the instrument visual indicators 80 on the console 32, the plug 42, the connector line 36, and the instrument 22. In the illustrated embodiment, the controller may activate the LEDs 206 to emit blue light through both light emitter portions 214, 216 to match the blue light emitted by the instrument visual indicators 80 on each one of the console 32, the plug 42, the connector line 36, and the footswitch 28.

The instrument visual indicators 80 coupled to the plug 42 of the first connector line 36 may comprise the light emitter 86 of FIG. 4 in the form of LED 92 and ring-shaped light guide 98. The LED 92 may comprise the multi-colored light emitter configured to emit a plurality of colored lights. The controller may activate the LED 92 to emit a colored light that matches a colored light emitted by any one or more of the footswitch visual indicators 162 on the console 32, the plug 52, the connector line 48, and/or the footswitch 28. In the illustrated embodiment, the controller 68 activates the LED 92 to emit a blue light to match the blue light emitted by the footswitch visual indicators 162 on each one of the console 32, the plug 52, the connector line 48, and the footswitch 28.

The footswitch visual indicators 162 coupled to the plug 52 of the connector line 48 may comprise the light emitter 170 of FIG. 8 in the form of the LED 174 and ring-shaped light guide 177. In the illustrated embodiment, the LED 174 may comprise the multi-colored light emitters configured to emit a plurality of colored lights. The controller 68 may activate the LED 174 to emit a colored light that matches the colored light emitted by any one or more of the instrument visual indicators 80 on the console 32, the plug 42, the connector line 36, and the instrument 22. In the illustrated embodiment, the controller 68 may activate the LED 174 to emit blue light to match the blue light emitted by the instrument visual indicators 80 on each one of the console 32, the plug 42, the connector line 36, and the footswitch 28.

Instrument visual indicators 80 integrated or embedded within one or both ends of the connector line may comprise the light emitter 104 of FIG. 5 in the form of the LEDs 110 and/or fiber optic/light strips 116 coupled to opposing ends of the connector line 36. In the illustrated embodiment, the LEDs 110 may comprise multi-colored light emitters configured to emit a plurality of colored lights. The controller may activate the LEDs 110 to emit a colored light that matches a colored light emitted by any one or more of the footswitch visual indicators 162 on the console 32, the plug 52, the connector line 48, and the footswitch 28. In the illustrated embodiment, the controller 68 activates the LEDs 110 to emit a blue light to match the blue light emitted by the footswitch visual indicators 162 on each one of the console 32, the plug 52, the connector line 48, and the footswitch 28.

Footswitch visual indicators 162 integrated or embedded within one or both ends of the connector line 48 may comprise the light emitters 178 of FIG. 9 in the form of the LEDs 182 and fiber optic strips 186 coupled to opposing ends of the connector line 48. In the illustrated embodiment, the LEDs 182 may comprise multi-colored light emitter configured to emit a plurality of colored lights. The controller 68 may activate the LEDs 182 to emit a colored light that matches the colored light emitted by any one or more of the instrument visual indicators 80 on the console 32, the plug 42, the connector line 36, and the instrument 22. In the illustrated embodiment, the controller 68 may activate the LEDs 182 to emit blue light to match the blue light emitted by the instrument visual indicators 80 on each one of the console 32, the plug 42, the connector line 36, and the footswitch 28.

Instrument visual indicators 80 integrated or embedded within the first handheld surgical instrument 22 may comprise the light emitters 122 of FIG. 6 in the form of the LED 128 and ring-shaped light guide 134. In the illustrated embodiment, the LED 128 may comprise a multi-colored light emitter configured to emit a plurality of colored lights. The controller 68 may activate the LED 128 to emit a colored light that matches a colored light emitted by any one or more of the footswitch visual indicators 162 on the console 32, the plug 52, the connector line 48, and the footswitch 28. In the illustrated embodiment, the controller 68 activates the LED 128 to emit a blue light to match the blue light emitted by the footswitch visual indicators 162 on each one of the console 32, the plug 52, the connector line 48, and the footswitch 28.

Footswitch visual indicators 162 integrated or embedded in the first footswitch 28 may comprise a light emitter 190 of FIG. 10 in the form of the LED 194 and ring-shaped light guide 198. In the illustrated embodiment, the LED 194 may comprise a multi-colored light emitter configured to emit a plurality of colored lights. The controller 68 may activate the LEDs 194 to emit a colored light that matches the colored light emitted by any one or more of the instrument visual indicators 80 on the console 32, the plug 42, the connector line 36, and the instrument 22. In the illustrated embodiment, the controller 68 may activate the LEDs 194 to emit blue light to match the blue light emitted by the instrument visual indicators 80 on each one of the console 32, the plug 42, the connector line 36, and the footswitch 28.

It is contemplated that the visual indicators on any one or more of the console 32, plugs, connector lines, instruments, and/or footswitches may take a variety of forms, including but not limited to, light emitters, fiber optic strips, displays, electromechanical devices, etc. For instance, if the visual indicator takes the form of the touchscreen panel or display 62 on the console 32, the display 62 can show a colored icon 74, symbol, illustration, or verbal description of the type of association that corresponds with the output of the footswitch visual indicator. In the illustrated embodiment, the controller 68 may activate the display 62 to show the icon 74 in a position that is aligned with or adjacent to the associated first instrument port 56, and in a color that matches the colored light emitted from the footswitch visual indicator 162. Other embodiments of the visual indicators may comprise any number or type of visual indicators coupled to any portion(s) of the console 32, plugs, connector lines, instruments, and/or footswitches. In addition, other embodiments of any one or more of the console 32, plugs, connector lines, instruments, and/or footswitches, which do not comprise visual indicators, are also contemplated.

Referring to FIGS. 15 and 16, the controller 68 associates the second instrument port 58 with the first footswitch port 64, and the controller 68 activates one or more instrument visual indicators 82 of the associated second instrument port 58 and one or more footswitch visual indicators 162 of the first footswitch port 64 to display outputs corresponding with one another. In the illustrated embodiment, the controller activates the instrument visual indicators 82 of the associated instrument port 58 and the footswitch visual indicator 162 of the first footswitch port 64 to emit colors that match one another. The first footswitch port 64, plug 52, connector line 48, footswitch 28, and footswitch visual indicators 162 may be similar to those provided in the description for FIGS. 13 and 14.

The instrument visual indicator 82 of the associated second instrument port 58 on the console 32 may comprise the light emitter 142 of FIG. 7 in the form of the LEDs 148 and ring-shaped light guide 154. The ring-shaped light guide 154 may be coupled to the console 32 and surround the second instrument port 58. The ring-shaped light guide 154 can comprise two arcuate light emitter portions 158, 160 on opposing sides of the second instrument port 58, with one light emitter portion 158 adjacent to the other light emitter portion 160. While FIG. 9 illustrates the light emitter portion 158 positioned above the light emitter portion 160 in a vertical arrangement, it is contemplated that the light emitter portions 158, 160 can be positioned lateral to one another in a side-by-side arrangement or in any other suitable arrangement. In this embodiment, each one of the LEDs 148 comprises a multi-colored light emitter configured to emit a plurality of colored lights. The controller may activate the LEDs 148 to emit a colored light through both light emitter portions 158, 160 that matches a colored light emitted by any one or more of the footswitch visual indicators 162 on the console 32, the plug 52, the connector line 48, and the footswitch 28. In the illustrated embodiment, the controller 68 activates the LEDs 148 to emit a blue light through both light emitter portions 158, 160 to match the blue light emitted by the footswitch visual indicators 162 on each one of the console 32, the plug 52, the connector line 48, and the footswitch 28.

The instrument visual indicator 82 coupled to the plug 44 may comprise the light emitter 88 of FIG. 4 in the form of the LED 94 and ring-shaped light guide 100. The LED 94 may comprise the multi-colored light emitter configured to emit a plurality of colored lights. The controller may activate the LED 94 to emit a colored light that matches a colored light emitted by any one or more of the footswitch visual indicators 162 on the console 32, the plug 52, the connector line 48, and the footswitch 28. In the illustrated embodiment, the controller 68 activates the LED 94 to emit a blue light to match the blue light emitted by the footswitch visual indicators 162 on each one of the console 32, the plug 52, the connector line 48, and the footswitch 28.

Instrument visual indicators 82 integrated or embedded within one or both ends of the connector line 38 may comprise the light emitter 106 of FIG. 5 in the form of the LEDs 112 and fiber optic strips 118 coupled to opposing ends of the connector line 38. In the illustrated embodiment, the LEDs 112 may comprise multi-colored light emitters configured to emit a plurality of colored lights. The controller may activate the LEDs 112 to emit a colored light that matches a colored light emitted by any one or more of the footswitch visual indicators 162 on the console 32, the plug 52, the connector line 48, and the footswitch 28. In the illustrated embodiment, the controller 68 activates the LEDs 112 to emit a blue light to match the blue light emitted by the footswitch visual indicators 162 on each one of the console 32, the plug 52, the connector line 48, and the footswitch 28.

Instrument visual indicators 82 integrated or embedded within the first handheld surgical instrument 24 may comprise the light emitter 124 of FIG. 6 in the form of the LED 130 and ring-shaped light guide 136. In the illustrated embodiment, the LED 130 may comprise a multi-colored light emitter configured to emit a plurality of colored lights. The controller may activate the LED 130 to emit a colored light that matches a colored light emitted by any one or more of the footswitch visual indicators 162 on the console 32, the plug 52, the connector line 48, and the footswitch 28. In the illustrated embodiment, the controller 68 activates the LED 130 to emit a blue light to match the blue light emitted by the footswitch visual indicators 162 on each one of the console 32, the plug 52, the connector line 48, and the footswitch 28.

It is contemplated that the visual indicators on any one or more of the console 32, plugs, connector lines, instruments, and/or footswitches may take a variety of forms, including but not limited to, light emitters, fiber optic strips, displays, electromechanical devices, etc. For instance, if the visual indicator takes the form of the touchscreen panel or display 62 on the console 32, the display 62 can show a colored icon 74, symbol, illustration, or verbal description of the type of association that corresponds with the output of the footswitch visual indicator. In the illustrated embodiment, the controller 68 may activate the display 62 to show the icon 74 in a position that is aligned with or adjacent to the associated first instrument port 56, and in a color that matches the colored light emitted from the footswitch visual indicator 162. Other embodiments of the visual indicators may comprise any number or type of visual indicators coupled to any portion(s) of the console 32, plugs, connector lines, instruments, and/or footswitches. In addition, other embodiments of any one or more of the console 32, plugs, connector lines, instruments, and/or footswitches, which do not comprise visual indicators, are also contemplated.

Figure 17:
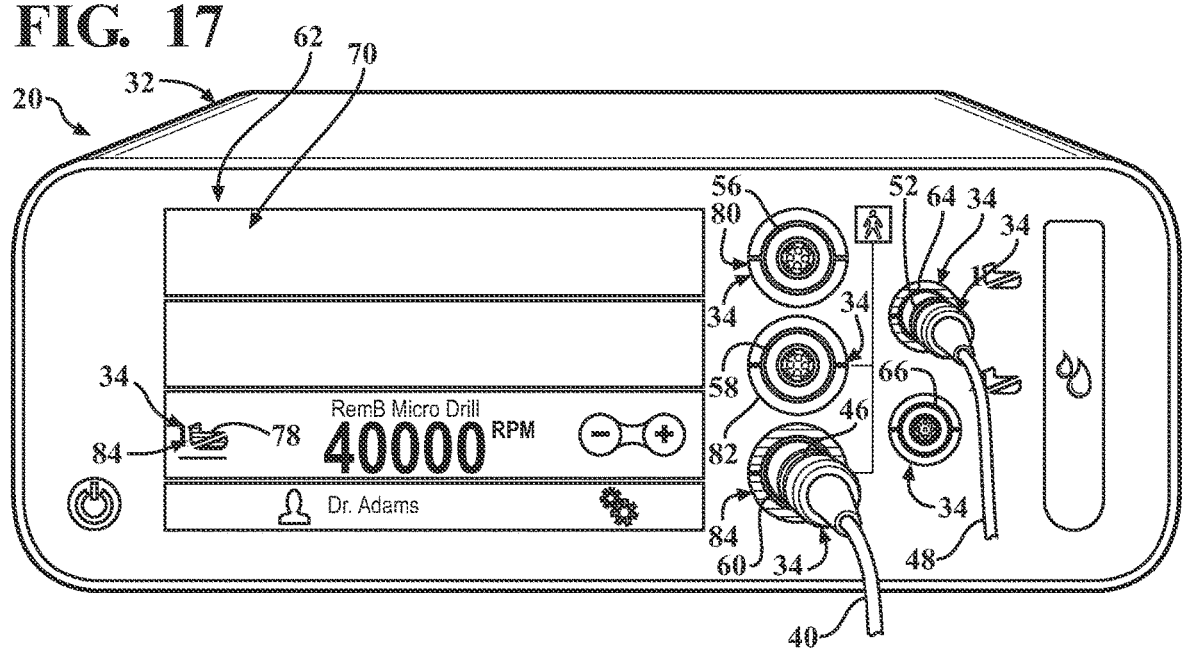
FIG. 17 is a front perspective view of the console of FIG. 3, illustrating the connector line of the third handheld surgical instrument coupled to the third instrument port and the connector line of the first footswitch coupled to the first footswitch port.
Figure 18:
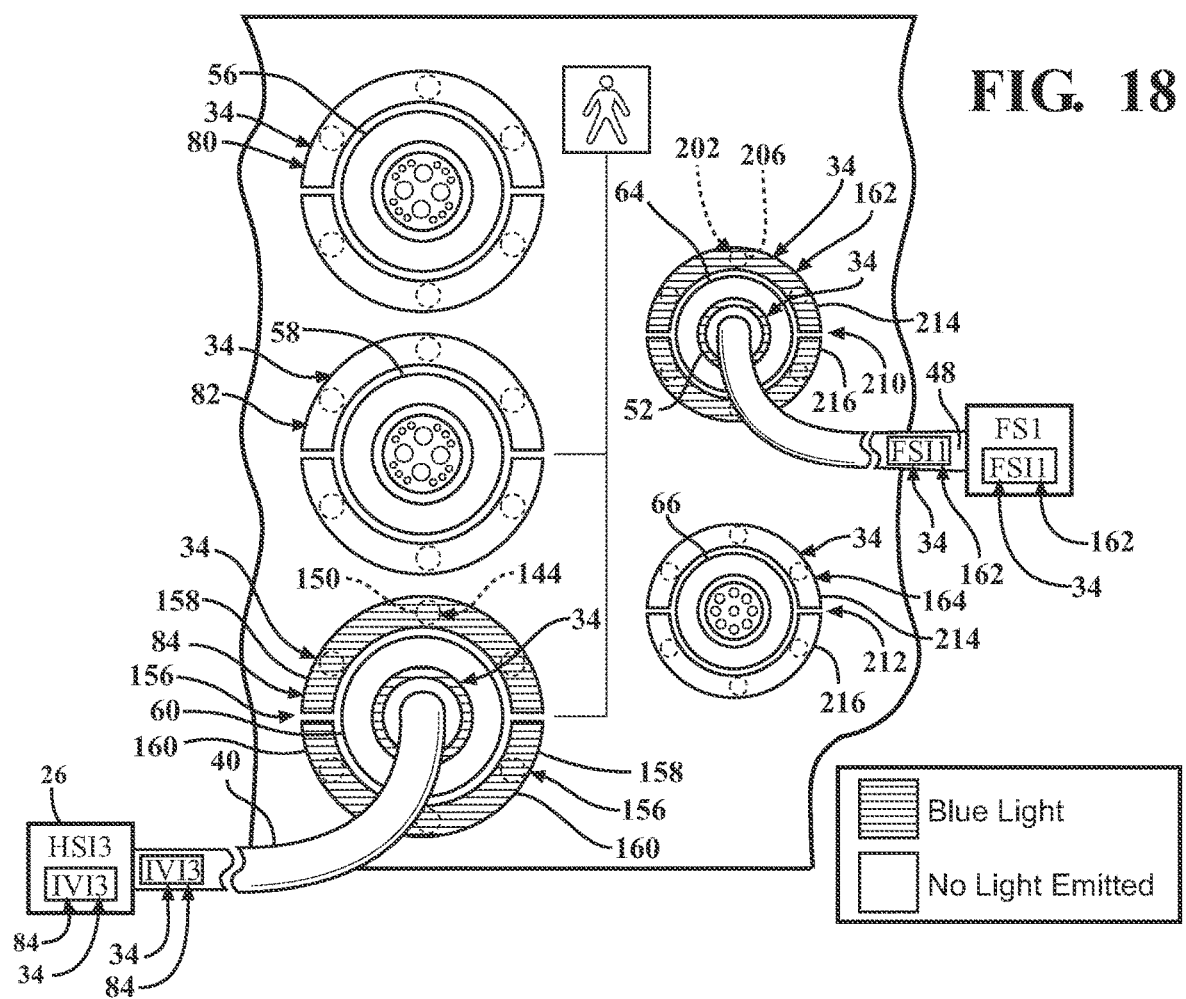
FIG. 18 is an enlarged view of the instrument ports and footswitch ports of FIG. 17, with an association between the third instrument port and the first footswitch port being indicated by a plurality of third instrument visual indicators and a plurality of first footswitch visual indicators.

Referring to FIGS. 17 and 18, the controller 68 associates the third instrument port 60 with the first footswitch port 64, and the controller 68 activates one or more instrument visual indicators 80 of the associated third instrument port 60 and one or more footswitch visual indicators 162 of the first footswitch port 64 to display outputs corresponding with one another. In the illustrated embodiment, the controller activates the instrument visual indicators 80 of the associated instrument port 60 and the footswitch visual indicator 162 of the first footswitch port 64 to emit colors that match one another. In the illustrated embodiment, the first footswitch port 64, plug 52, connector line 48, footswitch 28, and footswitch visual indicators 162 are similar to those provided in the description for FIGS. 13 and 14.

The instrument visual indicator 84 of the associated third instrument port 60 on the console 32 may comprise the light emitter 144 of FIG. 7 in the form of the LEDs 150 and ring-shaped light guide 156. The ring-shaped light guide 156 may be coupled to the console 32 and surround the third instrument port 60. The ring-shaped light guide 156 can comprise two arcuate light emitter portions 158, 160 on opposing sides of the third instrument port 60, with one light emitter portion 158 adjacent to the other light emitter portion 160. While FIG. 11 illustrates the light emitter portion 158 positioned above the light emitter portion 160 in a vertical arrangement, it is contemplated that the light emitter portions 158, 160 can be positioned lateral to one another in a side-by-side arrangement or in any other suitable arrangement. In this embodiment, each one of the LEDs 150 comprises a multi-colored light emitter configured to emit a plurality of colored lights. The controller may activate the LEDs 150 to emit a colored light through both light emitter portions 158, 160 that matches a colored light emitted by any one or more of the footswitch visual indicators 162 on the console 32, the plug 52, the connector line 48, and the footswitch 28. In the illustrated embodiment, the controller 68 activates the LEDs 150 to emit a blue light through both light emitter portions 158, 160 to match the blue light emitted by the footswitch visual indicators 162 on each one of the console 32, the plug 52, the connector line 48, and the footswitch 28.

The instrument visual indicator 84 coupled to the plug 46 may comprise the light emitter 90 of FIG. 4 in the form of LED 96 and ring-shaped light guide 102. The LED 96 may comprise multi-colored light emitters configured to emit a plurality of colored lights. The controller may activate the LEDs 96 to emit a colored light that matches a colored light emitted by any one or more of the footswitch visual indicators 162 on the console 32, the plug 52, the connector line 48, and the footswitch 28. In the illustrated embodiment, the controller activates the LED 96 to emit a blue light to match the blue light emitted by the footswitch visual indicators 162 on each one of the console 32, the plug 52, the connector line 48, and the footswitch 28.

Instrument visual indicators 84 integrated or embedded within one or both ends of the connector line 40 may comprise the light emitters 108 of FIG. 5 in the form of the LEDs 114 and fiber optic strips 120 coupled to opposing ends of the connector line 40. In the illustrated embodiment, the LEDs 114 may comprise multi-colored light emitters configured to emit a plurality of colored lights. The controller may activate the LEDs 114 to emit a colored light that matches a colored light emitted by any one or more of the footswitch visual indicators 162 on the console 32, the plug 52, the connector line 48, and the footswitch 28. In the illustrated embodiment, the controller activates the LEDs 114 to emit a blue light to match the blue light emitted by the footswitch visual indicators 162 on each one of the console 32, the plug 52, the connector line 48, and the footswitch 28.

Instrument visual indicators 84 integrated or embedded within the third handheld surgical instrument 26 may comprise the light emitter 126 of FIG. 6 in the form of the LED 132 and ring-shaped light guide 138. In the illustrated embodiment, the LED 132 may comprise the multi-colored light emitter configured to emit a plurality of colored lights. The controller may activate the LED 132 to emit a colored light that matches a colored light emitted by any one or more of the footswitch visual indicators 162 on the console 32, the plug 52, the connector line 48, and the footswitch 28. In the illustrated embodiment, the controller activates the LED 132 to emit a blue light to match the blue light emitted by the footswitch visual indicators 162 on each one of the console 32, the plug 52, the connector line 48, and the footswitch 28.

It is contemplated that the visual indicators on any one or more of the console 32, plugs, connector lines, instruments, and/or footswitches may take a variety of forms, including but not limited to, light emitters, fiber optic strips, displays, electromechanical devices, etc. For instance, if the visual indicator takes the form of the touchscreen panel or display 62 on the console 32, the display 62 can show a colored icon 74, symbol, illustration, or verbal description of the type of association that corresponds with the output of the footswitch visual indicator. In the illustrated embodiment, the controller 68 may activate the display 62 to show the icon 74 in a position that is aligned with or adjacent to the associated first instrument port 56, and in a color that matches the colored light emitted from the footswitch visual indicator 162. Other embodiments of the visual indicators may comprise any number or type of visual indicators coupled to any portion(s) of the console 32, plugs, connector lines, instruments, and/or footswitches. In addition, other embodiments of any one or more of the console 32, plugs, connector lines, instruments, and/or footswitches, which do not comprise visual indicators, are also contemplated.

Referring to FIGS. 19 and 20, the system 20 has a similar configuration as the one illustrated in FIGS. 13 and 14 because the system 20 includes connector 48, 36 coupled to the footswitch port 64 and the associated instrument port 56. More specifically, as described above, the controller activates the footswitch visual indicators 162 on the console 32, plug 52, connector line 48, and footswitch 28 and the instrument visual indicators 80 on the associated instrument port 56 of the console 32, the plug 42, to display outputs that correspond with one another to indicate the mapping between the ports 64, 56.

Furthermore, in FIGS. 19 and 20, the system 20 may include a second footswitch connector line 50 for a second footswitch 30 being connected to the second footswitch port 66, and the second connector line 38 for the second instrument 24 being connected to the second instrument port 58. The controller 68 may associate the second instrument port 58 with the second footswitch port 66. The controller may activate the second footswitch visual indicators 164 for the second footswitch port 66, second plug 54, second connector line 50, and/or second footswitch 30 and the second instrument visual indicators 82 for the associated second instrument port 58, second plug 44, second connector line 38, and/or second instrument 24 to display outputs that correspond with one another to indicate the association between the ports 66, 58. In the illustrated embodiment, the controller may activate the LEDs 208 of the second footswitch visual indicator 164 to emit a colored light, and the controller 68 may activate the LEDs 148 of the instrument visual indicator 82 to emit a colored light that matches the colored light emitted by the LEDs 208. More specifically, in the illustrated embodiment, the controller 68 may activate the LEDs 208, 148 to emit orange light to indicate that the ports 58, 66 are associated with one another.

Figure 21:
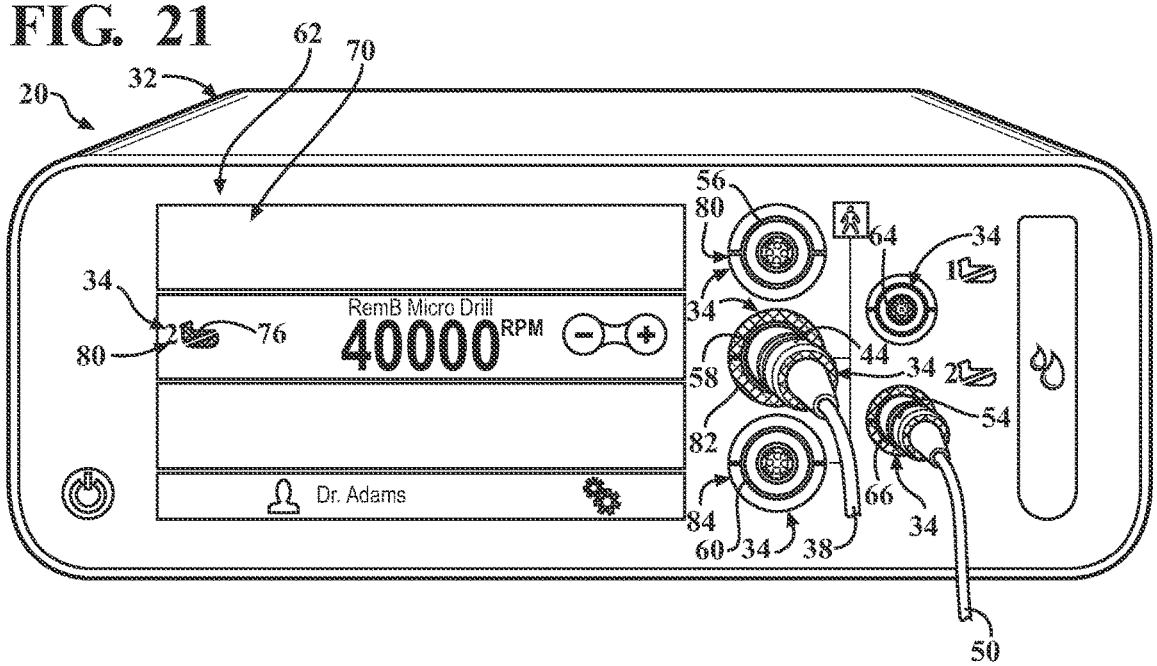
FIG. 21 is a front perspective view of the console of FIG. 3, illustrating the connector line of the second handheld surgical instrument coupled to the second instrument port and the connector line of the second footswitch coupled to the second footswitch port.
Figure 22:
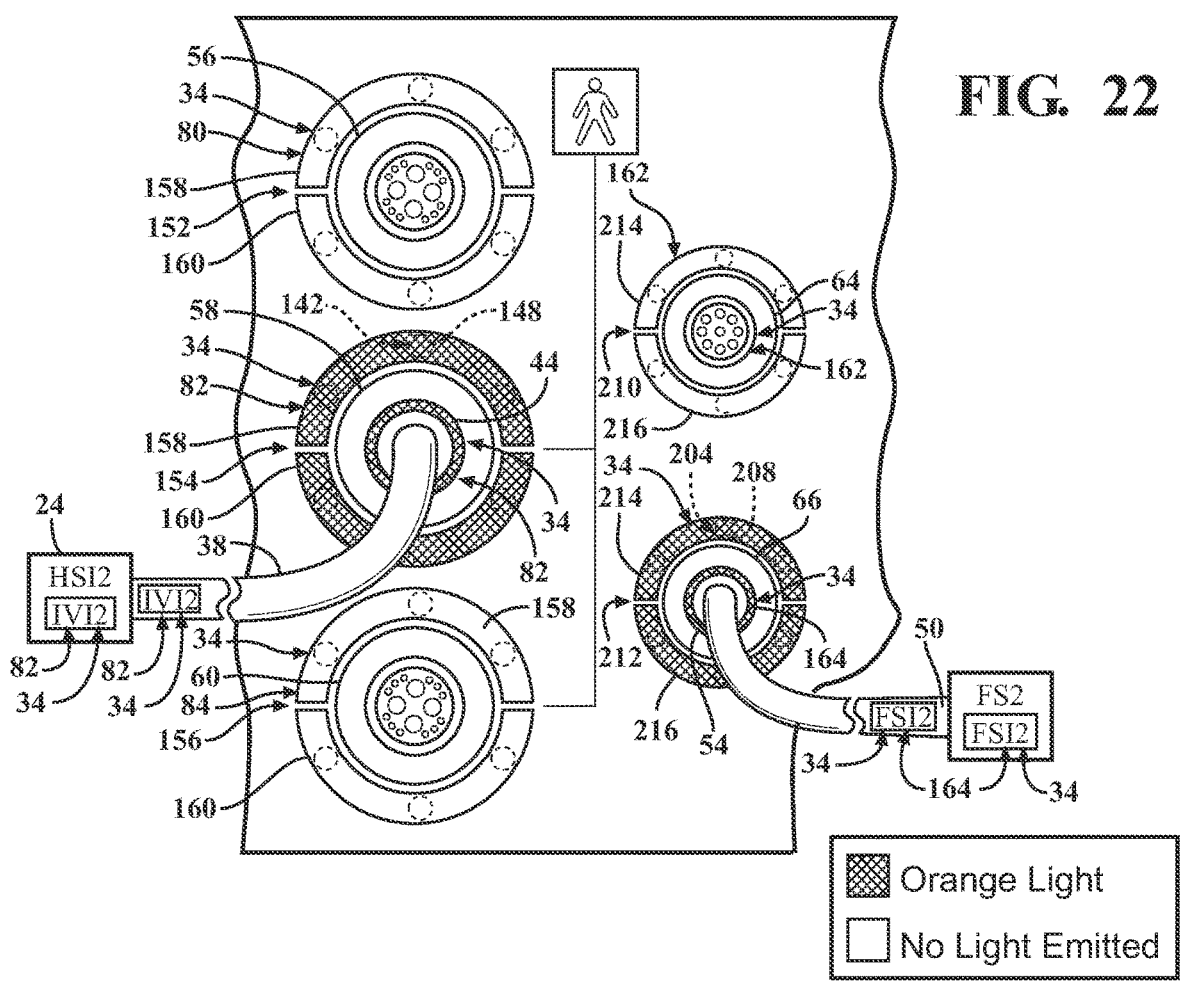
FIG. 22 is an enlarged view of the instrument ports and footswitch ports of FIG. 21, with an association between the second instrument port and the second footswitch port being indicated by a plurality of second instrument visual indicators and a plurality of second footswitch visual indicators.

Referring to FIGS. 21 and 22, the system 20 is disposed in a configuration similar to the one illustrated in FIGS. 19 and 20. However, while FIGS. 19 and 20 illustrate connector lines 48, 36 coupled to a respective one of the footswitch port 64 and the associated instrument port 56, the system illustrated in FIGS. 14 and 15 does not comprise the connector lines 48, 36. The footswitch port 64 is not associated with the instrument port 56, and the footswitch visual indicator 162 of the footswitch port 64 and the instrument visual indicator 80 of the instrument port 56 do not emit any light.

Figure 23:
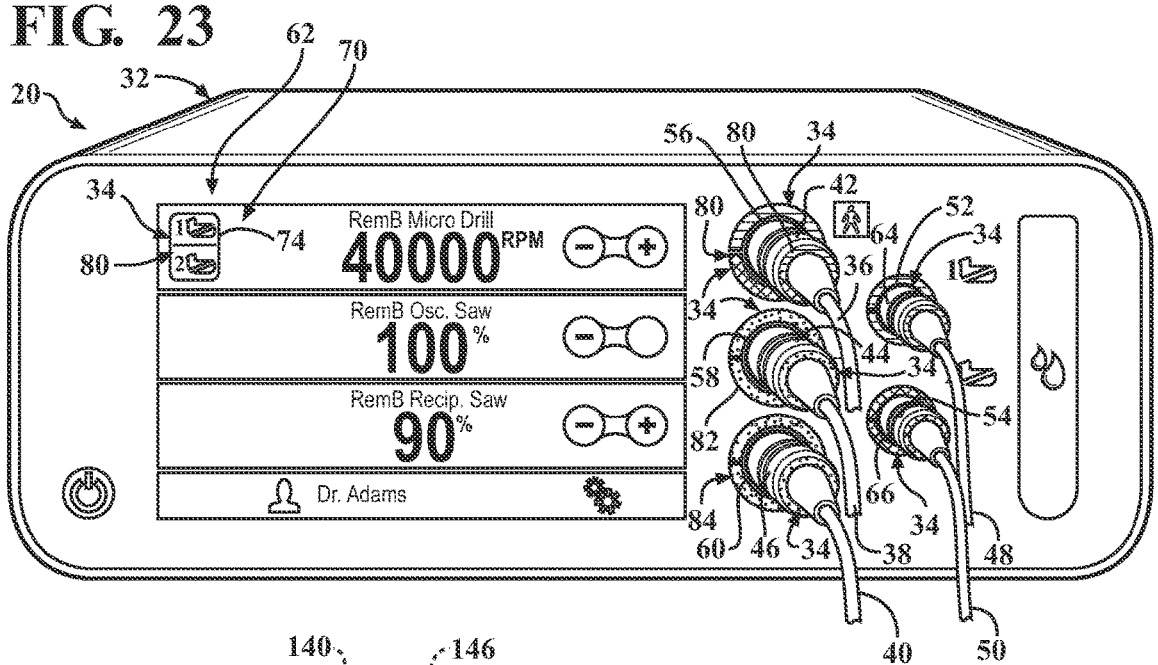
FIG. 23 is a front perspective view of the console of FIG. 3, illustrating the connector lines of the first, second, and third handheld surgical instruments coupled to a respective one of the first, second, and third instrument ports, and the connector lines of the first, second, and third footswitches coupled to a respective one of the first, second, and third footswitch ports.
Figure 24:
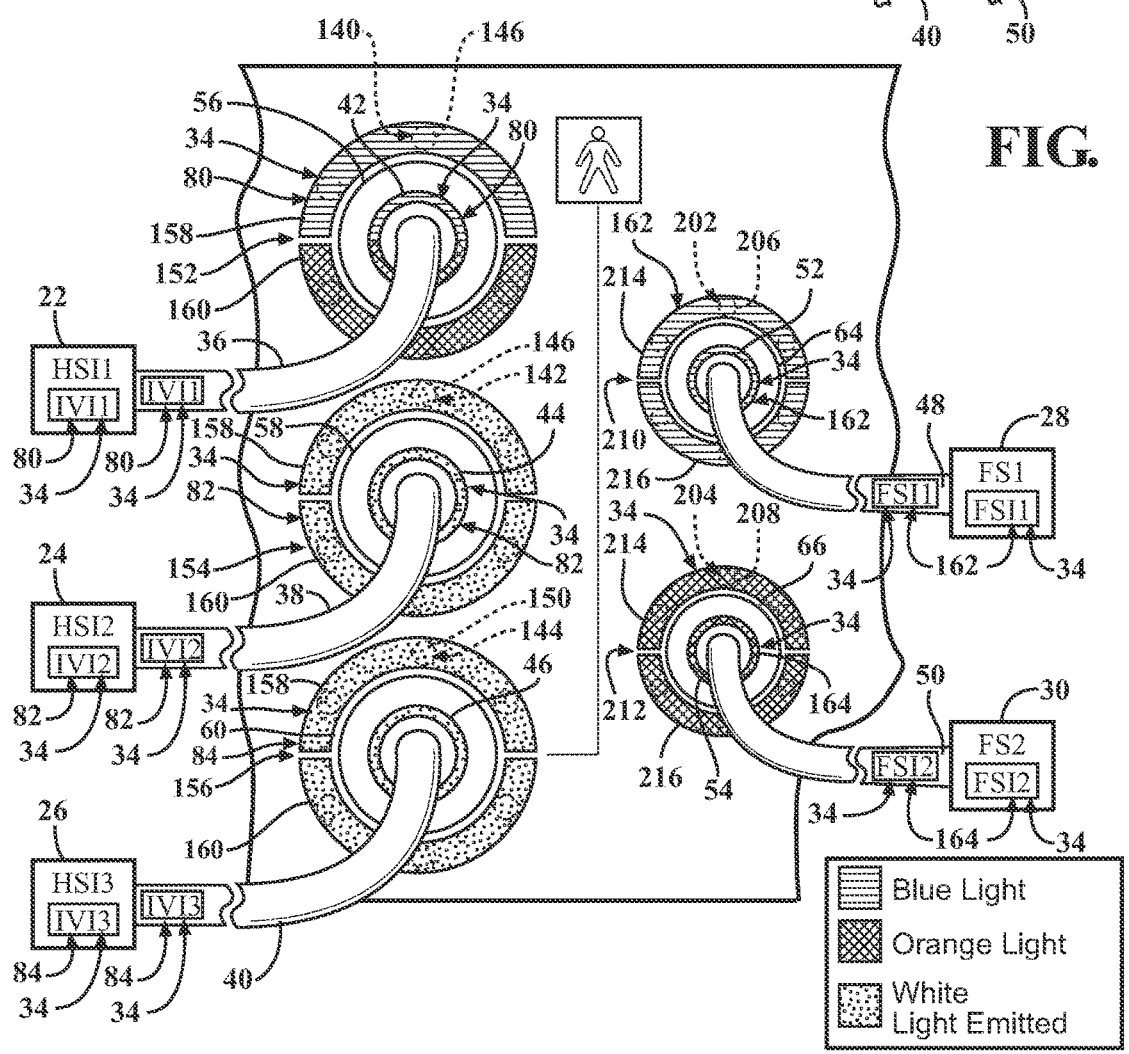
FIG. 24 is an enlarged view of the instrument ports and footswitch ports of FIG. 16, with an association between the first instrument port and the first and second footswitch ports being indicated by the first instrument visual indicators and the first and second footswitch visual indicators.

Referring to FIGS. 23 and 24, the system 20 may disposed in dual control mode. While the system 20 may be configured similar to the one illustrated in FIGS. 19 and 20, the system 20 associates the first instrument port 56 with both the first and second footswitch ports 64, 66. In addition, the system 20 activates the first footswitch visual indicator 162 of the first footswitch port 64 to emit blue light, the second footswitch visual indicator 82 of the second footswitch port 66 to emit orange light, and the first instrument visual indicator 80 of the associated first instrument port 56 to emit blue light and orange light to indicate that the associated instrument port 56 is associated with the first and second footswitch ports 162, 164. While the system of FIGS. 23 and 24 further includes second and third connector lines 38, 40 of second and third instruments 24, 26 being connected to the second and third the instrument ports 58, 60, the controller does not associate the second and third instrument ports 58, 60 with either one of the footswitch ports 64, 66. Furthermore, the controller 68 activates the second and third instrument visual indicators 82, 84 on the second and third instrument ports 58, 60, second and third plugs 44, 46, second and third connector lines 38, 40, and second and third instruments 24, 26 to emit white light to indicate that the second and third instrument ports 58, 60 are not associated with either one of the footswitch ports 64, 66.

Figure 25:
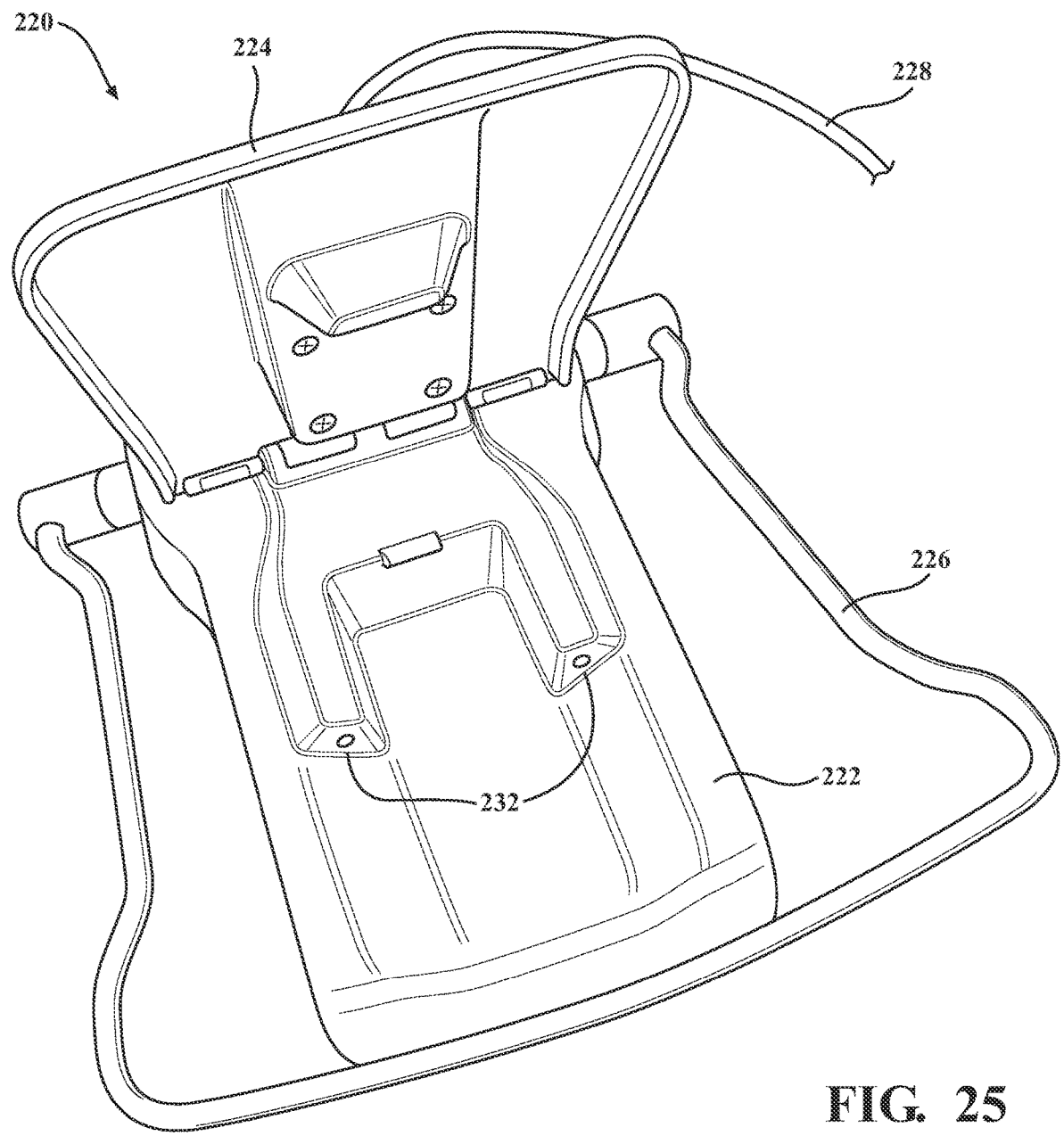
FIG. 25 is a perspective view of an exemplary footswitch shown in an open position.

Referring to FIGS. 25-28, an exemplary footswitch may be configured for use with system 20. Referring now to FIG. 25, a perspective view of a footswitch 220 is shown in an open position. It will be understood that the footswitch 220 may be used in system 20 in place of one or more of the footswitches 28, 30. The footswitch 220 may comprise a base 222, a pedal 224, and a carrying handle 226. The carrying handle 226 may be coupled to the base 222 and may be used to reposition the footswitch 220 or to transport the footswitch 220 from one location to another. The footswitch may be coupled to system 220 by a connector line 228 (which may be similar to one of connector lines 48, 50, as described more fully above with reference to FIG. 1).

Figure 26:
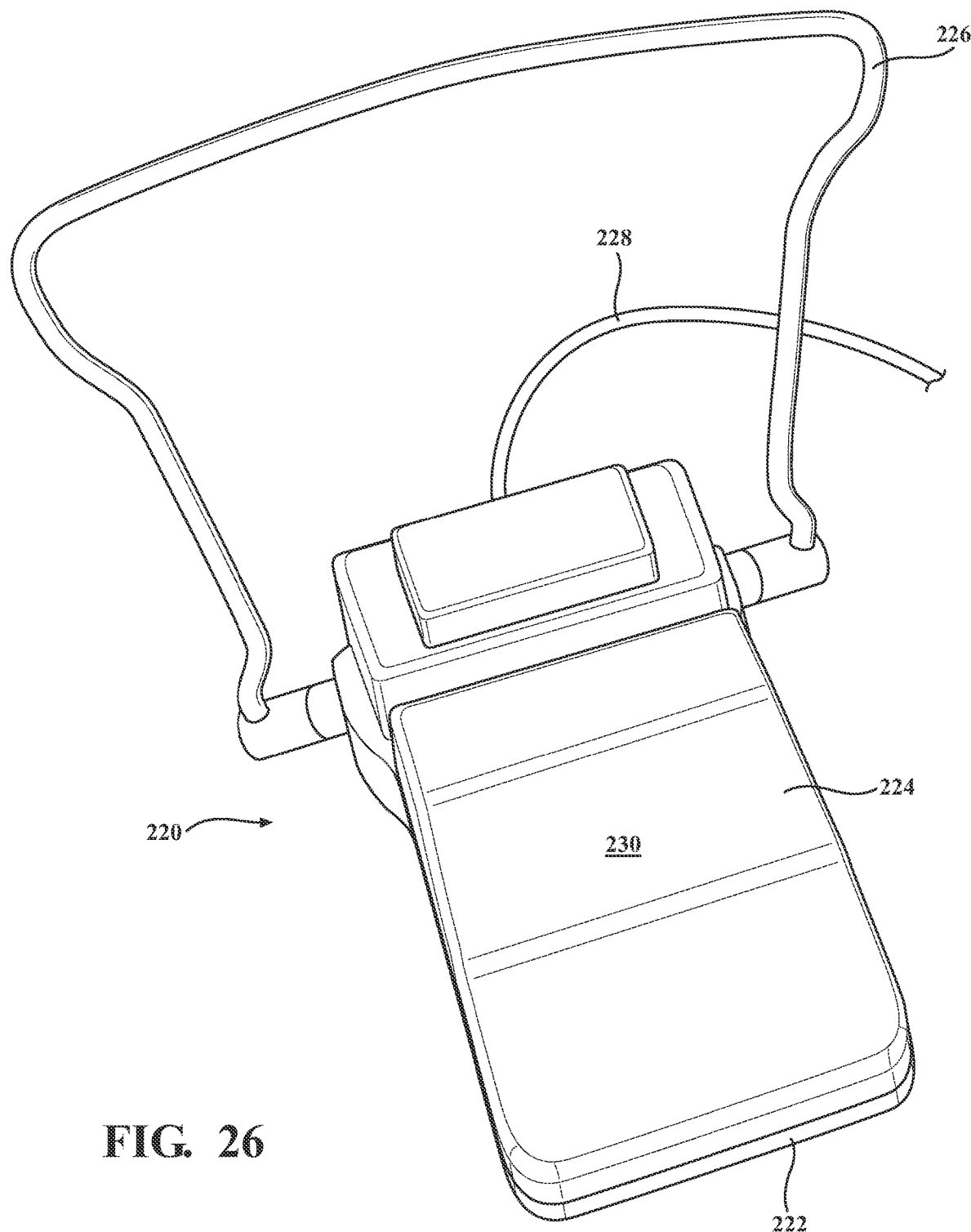
FIG. 26 is a perspective view of the footswitch of FIG. 25, shown in a closed position.

Referring now to FIG. 26, a perspective view of the footswitch 220 in a closed position is shown. The pedal 224 may be movably coupled to the base 222. In the closed position, the pedal 224 may overlay and/or completely or partially cover the base 222. The foot pedal 224 may comprise a substantially flat surface 230 upon which a user's foot may rest, which may activate the footswitch 220.

Figure 27:
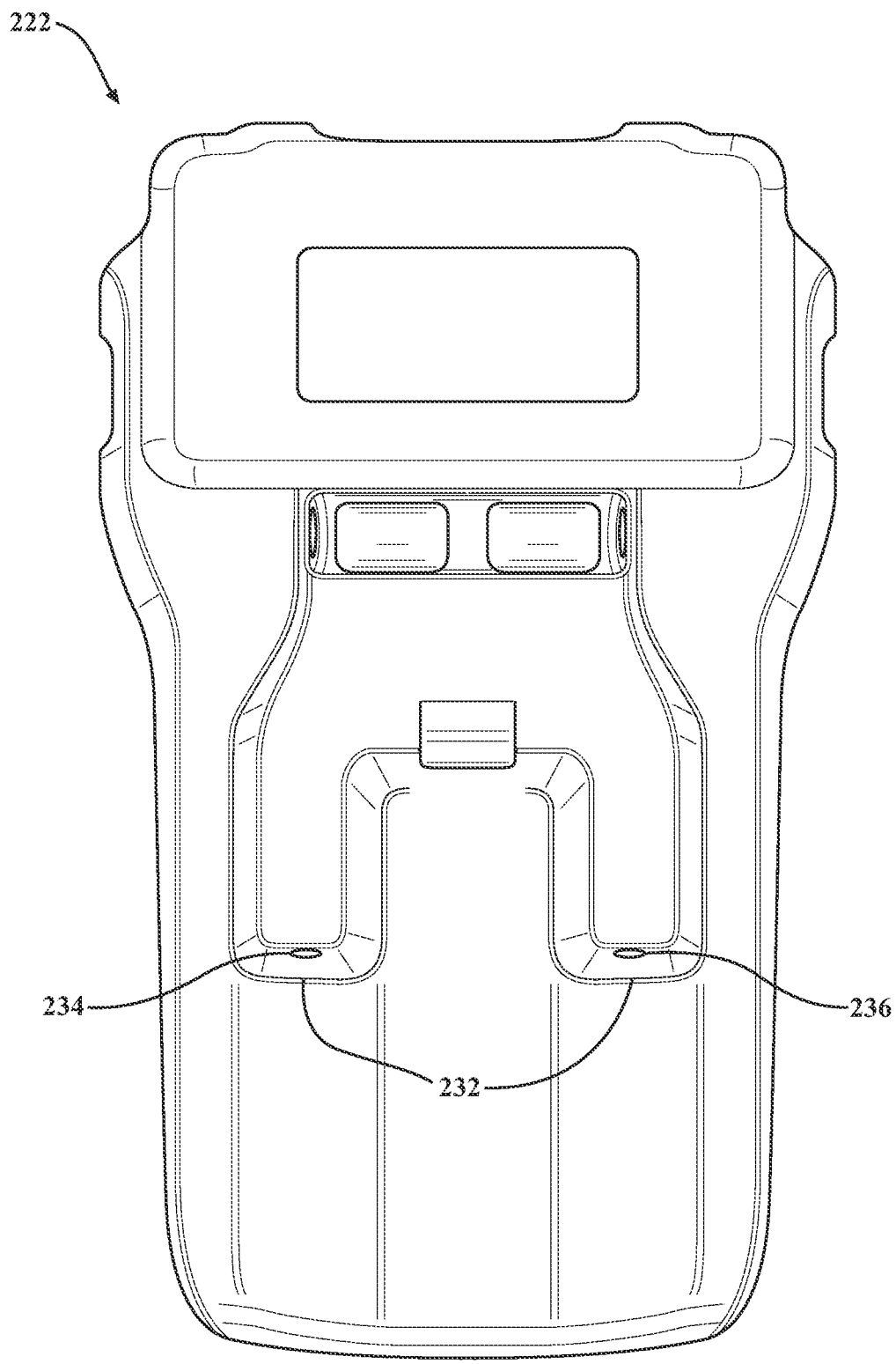
FIG. 27 is a top view of a base of the footswitch of FIGS. 25 and 26.

Referring now to FIG. 27, a top view of the base 222 is illustrated. The base 222 may comprise one or more input visual indicators 232. In some embodiments, the input visual indicators 232 may function similarly to the plurality of visual indicators 34 and/or 162, 164, described more fully above. For instance, when the footswitch 220 is used in place of one or more of footswitches 28, 30, input visual indicators 232 may indicate which of the instruments 22, 24, 26 and footswitches 28, 30 correspond with one another. For instance, in an exemplary embodiment, the controller activates the instrument visual indicators 80 of the associated first instrument port 56 and the footswitch visual indicators 162 of the first footswitch port 64 to emit colors that match one another, and the input visual indicators 232 are additionally activated by the controller to emit matching colors. The input visual indicators 232 may take a variety of forms, including but not limited to, light emitters, fiber optic strips, displays, electromechanical devices, etc. In some embodiments, the input visual indicators 232 may comprise a plurality of footswitch light emitters. By way of example, in the illustrated embodiment, the input visual indicators 232 comprise a first footswitch light emitter 234 and a second footswitch light emitter 236. The first footswitch light emitter 234 may be configured to output light of a first color. The second footswitch light emitter 236 may be configured to output light of a second color. In some embodiments, the first color and second color may be different from one another. In other embodiments, the first color and the second color may be the same color. Alternatively still, the footswitch light emitters 234, 236 may each be configured to output two or more colors of light.

Figure 28:
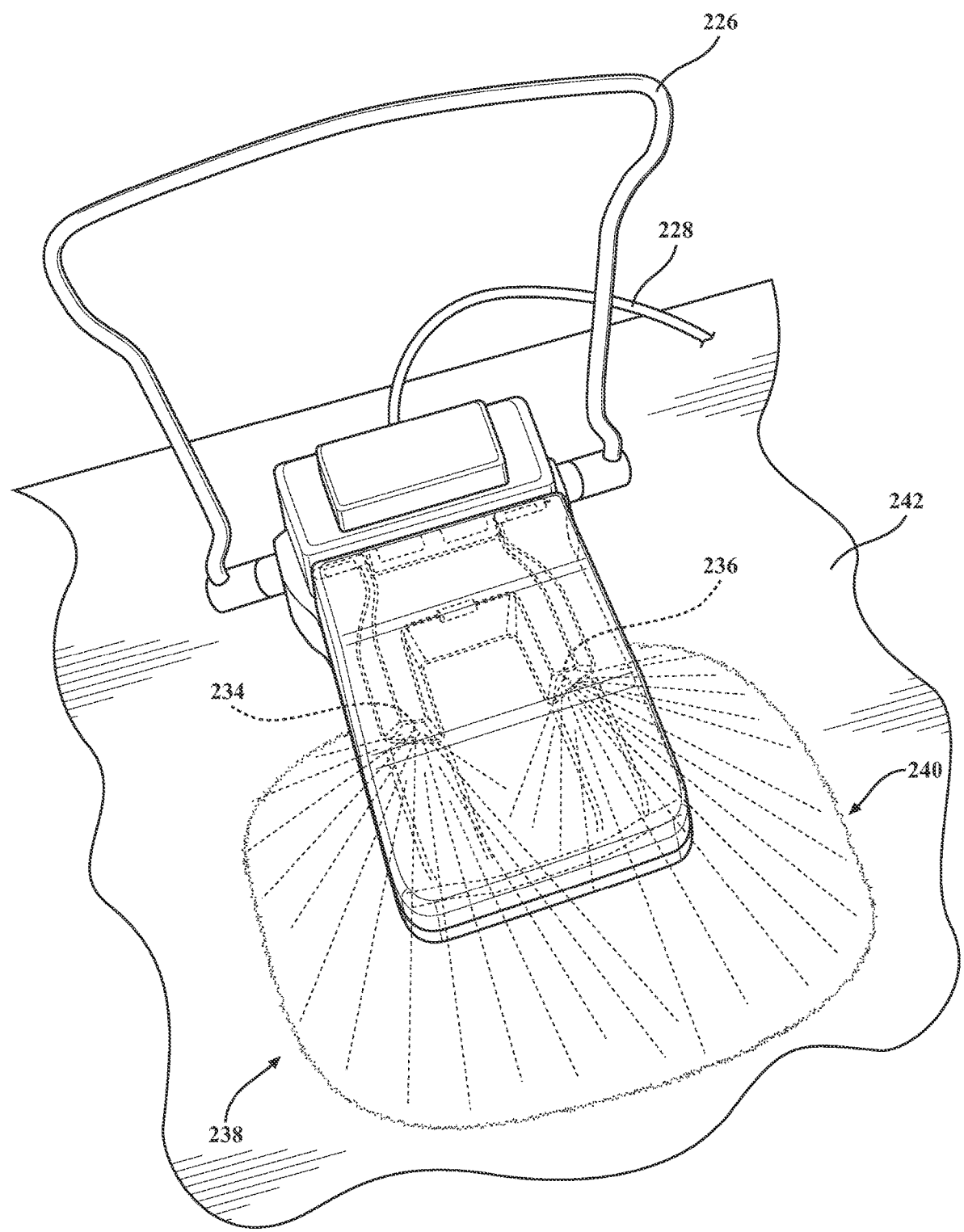
FIG. 28 is a top plan view of the footswitch of FIGS. 25 and 26 shown in the closed position.

Referring now to FIG. 28, a top plan view of the footswitch 220 in the closed position is illustrated. The first footswitch light emitter 234 is illustrated in an "on" mode, emitting light shown generally in dashed lines as a first output light 238. The second footswitch light emitter 236 is also illustrated in an "on" mode, emitting light shown generally in dashed lines as a second output light 240. The first output light 238 and the second output light 240 illuminate a surface 242, which may be the floor of a surgical suite or other suitable location for using the footswitch 220. Illumination of the surface 242 with the first and second output lights 238, 240 provides an immediate visual indication to the user of the color associated with the footswitch 220, and therefore of the instrument being activated by the footswitch 220. This may be particularly useful in environments with low ambient light.

During operation, the controller will selectively illuminate only one of the first output light 238 and second output light 240. For example, if the instrument port 56 and the footswitch visual indicators 162 of the first footswitch port 64 are both illuminated in a blue color, the controller will cause the first output light 238 and/or the second output light to output a blue color. This allows a user to readily determine the mapping of the footswitch without looking at the console. Similarly, if the system uses a second footswitch having the configuration of footswitch 220, the controller may cause the first and second output lights to output a different color light, indicating that the second footswitch is mapped to a different instrument than the first footswitch. The second instrument port visual indicator and the second footswitch visual indicator may output a light that matches this different color light.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

Embodiments of the disclosure can be described with reference to the following numbered clauses, with specific features laid out in the dependent clauses:

I. A console-based surgical system comprising:
  a plurality of handheld surgical instruments, each instrument having a connector line and an instrument visual indicator coupled to one of said instrument and said connector line;
  a footswitch having a connector line and a footswitch visual indicator coupled one of said footswitch and said connector line; and
  a console comprising:
    a plurality of instrument ports, said connector lines of said plurality of handheld instruments being connected to said plurality of instrument ports;
    a footswitch port, said connector line of said footswitch connected to said footswitch port; and
    a controller configured to associate said footswitch port with one of said instrument ports such that said footswitch is operable to actuate a function of said handheld surgical instrument connected to said associated instrument port;
    said controller further configured to activate said footswitch visual indicator and said instrument visual indicator of said associated instrument port and associated footswitch port to display outputs that correspond with one another.

II. The console-based surgical system of clause I wherein each one of said instrument visual indicator and said footswitch visual indicator comprises a light emitter.

III. The console-based surgical system of claim II wherein said light emitter of one of said instrument visual indicator and said footswitch visual indicator comprises a ring-shaped light guide.

IV. The console-based surgical system of any one of clauses II or III wherein said light emitters of said footswitch visual indicator and said instrument visual indicator are configured to emit colors that match one another when said footswitch visual indicator and said instrument visual indicator display outputs that correspond with one another.

V. The console-based surgical system of any one of clauses II, III, or IV, wherein said light emitter comprises at least one of a LED, a fiber optic, and combinations thereof.

VI. The console-based surgical system of any one of the preceding clauses further comprising a user input device coupled to the controller and actuatable by a user to output a user output signal to cause said controller to associate said footswitch port with said associated instrument port.

VII. The console-based surgical system of any one of the preceding clauses further comprising:
  a second footswitch having a connector line and a second footswitch visual indicator coupled one of said second footswitch and said connector line;

said console further comprising a second footswitch port, said connector line of said second footswitch connected to said second footswitch port;

said controller further configured to associate said second footswitch port with said associated instrument port such that said second footswitch is operable to actuate said function of said handheld surgical instrument connected to said associated instrument port; and said controller further configured to activate said second footswitch visual indicator and said instrument visual indicator of said associated instrument port to display outputs that correspond with one another.

VIII. The console-based surgical system of any one of clause VII further comprising:

a third footswitch visual indicator coupled to a portion of said console adjacent to said footswitch port;

a fourth footswitch visual indicator coupled to a portion of said console adjacent to said second footswitch port;

a second instrument visual indicator coupled to said console adjacent to a first instrument port of said plurality of instrument ports;

a third instrument visual indicator coupled to said console adjacent to a second instrument port of said plurality of instrument ports; and a fourth instrument visual indicator coupled to said console adjacent to a third instrument port of said plurality of instrument ports;

said controller further configured to associate at least one of said footswitch port and second footswitch port with at least one of said first instrument port, said second instrument port, and said third instrument port, such that at least one of said first footswitch and said second footswitch is operable to actuate said function of said handheld surgical instrument connected to one of said first instrument port, said second instrument port, and said third instrument port; and said controller further configured to activate said third footswitch visual indicator, said fourth footswitch visual indicator, said second instrument visual indicator, and said third instrument visual indicator to display outputs that correspond with one another.

IX. The console-based surgical system of clause VIII wherein each one of said footswitch visual indicator, said second footswitch visual indicator, said third footswitch visual indicator, said fourth footswitch visual indicator, said instrument visual indicator, said second instrument visual indicator, said third instrument visual indicator, and said fourth instrument visual indicator comprises a light emitter.

X. The console-based surgical system of clause IX wherein said light emitter comprises a ring-shaped light guide.

XI. The console-based surgical system of any one of clauses IX or X wherein said light emitters are configured to emit colors that match one another when said footswitch visual indicator, said instrument visual indicator, said second footswitch visual indicator, said third footswitch visual indicator, said fourth footswitch visual indicator, said second instrument visual indicator, and said third instrument visual indicator display outputs that correspond with one another.

XII. The console-based surgical system of any one of clauses IX, X, or XI wherein said light emitter of said footswitch visual indicator is configured to emit a first colored light, said light emitter of said second footswitch visual indicator is configured to emit a second colored light, and said light emitter of said instrument visual indicator for said associated instrument port is configured to emit said first colored light and said second colored light when said footswitch visual indicator, said second footswitch visual indicator, and said instrument visual indicator of said associated instrument port display outputs that correspond with one another.

XIII The console-based surgical system of any one of clauses IX, X, or XI wherein said light emitter of said third footswitch visual indicator is configured to emit a first colored light, said light emitter of said fourth footswitch visual indicator is configured to emit a second colored light, and said light emitter of said second instrument visual indicator for said first instrument port is configured to emit said first colored light and said second colored light when said third footswitch visual indicator, said fourth footswitch visual indicator, and said second instrument visual indicator of said associated instrument port display outputs that correspond with one another.

XIV. The console-based surgical system of any one of clauses IX, X, XI, XII, or XIII wherein said light emitter of at least one of said first instrument port, said second instrument port, and said third instrument port comprises two light emitter portions with one of said light emitter portions adjacent to the other of said light emitter portions.

XV. The console-based surgical system of clause XIV wherein each one of said light emitter portions comprises a multi-colored light emitter configured to emit a plurality of colored lights.

XVI. The console-based surgical system of any one of the preceding clauses further comprising an input visual indicator coupled to at least one of said footswitch and said connector line coupled thereto.

XVII. The console-based surgical system of clause XVI wherein said controller is configured to activate said input visual indicator and said footswitch visual indicator to display outputs that correspond with one another.

XVIII. The console-based surgical system of any one of the preceding clauses further comprising an output visual indicator coupled to at least one of said handheld surgical instruments and said connector lines coupled thereto.

XIX. The console-based surgical system of clause XVIII wherein said controller is configured to activate said output visual indicator and said instrument visual indicator of said associated instrument port to display outputs that correspond with one another.

XX. A method of operating a console based surgical system, the console-based surgical system including a plurality of handheld surgical instruments, each instrument having a connector line and an instrument visual indicator coupled one of the instrument and the connector line, a footswitch having a connector line and a footswitch visual indicator coupled one of the footswitch and the connector line, a console including a plurality of instrument ports, the connector lines of the plurality of handheld instruments being connected to the plurality of instrument ports, the console further including a footswitch port, the connector line of the footswitch being connected to the footswitch port, and the console further including a controller, the method comprising:

associating the footswitch port to the instrument port such that the footswitch is operable actuate a function of the handheld surgical instrument connected to said associated instrument port; and activating the footswitch visual indicator and the instrument visual indicator of the associated instrument port to display outputs that correspond with one another.

XXI. The method of clause XX further comprising emitting colors from the footswitch visual indicator and the instrument visual indicator of the associated instrument port, with the colors matching one another.

XXII. The method of any one of clauses XX or XXI further comprising actuating a user input device to generate a user output signal to the controller to cause the controller to associate the footswitch port to the associated instrument port.

XXIII The method of clause XXII, the system further comprising a second footswitch having a connector line and a second footswitch visual indicator coupled one of the second footswitch and the connector line, the console further comprising a second footswitch port, the connector line of the second footswitch connected to the second footswitch port, the method comprising:

associating the second footswitch port with the associated instrument port such that the second footswitch is operable actuate a second function of the handheld surgical instrument connected to the associated instrument port; and activating the footswitch visual indicator, the second footswitch visual indicator, and the instrument visual indicator of the associated instrument port to display outputs that correspond with one another.

XXIV. The method of clause XXIII further comprising actuating said user input device to generate a second user output signal to associate the second footswitch port with the instrument port.

XXV. The method of any one of clauses XXIII or IIVI further comprising emitting colors from the footswitch visual indicator, the second footswitch visual indicator, and the instrument visual indicator of the associated instrument port, with the colors matching one another.

XXVI. The method of any one of clauses XXIII, XXIV, or XXV further comprising:

emitting a first colored light from the footswitch visual indicator;

emitting a second colored light from the second footswitch visual indicator; and emitting the first colored light and the second colored light from the instrument visual indicator of the associated instrument port.

XXVII. The method of any one of the preceding clauses further comprising:

activating a second footswitch visual indicator coupled to the console adjacent to the footswitch port of the console; and activating a second instrument visual indicator coupled to the console adjacent to the one of the instrument ports of the console.

XXVIII. A console-based surgical system comprising:

a plurality of handheld surgical instruments, each of said instruments having a connector line;

a footswitch having a connector line; and a console comprising:

a plurality of instrument ports, each of said of instrument ports having an instrument visual indicator, said connector lines of said plurality of handheld instruments being connected to said plurality of instrument ports;

a footswitch port having a footswitch visual indicator, said connector line of said footswitch being connected to said footswitch port; and a controller configured to associate said footswitch port with one of said instrument ports such that said footswitch is operable to actuate a function of said handheld surgical instrument connected to said associated instrument port;

said controller further configured to activate said footswitch visual indicator and said instrument visual indicator of said associated instrument port and said associated footswitch port to display outputs that correspond with one another;

wherein each of said footswitch visual indicator and said instrument visual indicators comprises a light emitter, each of said light emitter and a ring shaped light guide coupled to said console to surround a corresponding one of said footswitch port and said instrument ports.

XXIX. The console-based surgical system of clause XXVIII wherein said controller activates said light emitter of one of said instrument visual indicators to emit a colored light to match a colored light emitted by said footswitch visual indicator when said controller associates said footswitch port with said associated instrument port such that said footswitch is operable to actuate a function of said handheld surgical instrument connected to said associated instrument port.

XXX. The console-based surgical system of clause XXIX wherein said controller activates said light emitter of the other one of said instrument visual indicators to emit white light to indicate that said instrument port is not associated with said footswitch port.

XXXI. The console-based surgical system of clause XXVIII wherein each of said ring-shaped light guide comprises two arcuate light emitter portions on opposing sides of the corresponding footswitch port and said instrument ports.

XXXII. The console-based surgical system of clause XXXI wherein each of said arcuate light emitter portions angularly extends approximately 180 degrees.

XXXIII. The console-based surgical system of clause XXXI wherein at least one of said light emitters is a multi-colored light emitter configured to emit a plurality of colors.

XXXIV. A surgical console comprising a plurality of instrument ports, a footswitch port and a controller configured to associate said footswitch port with one of said instrument ports such that said footswitch is operable to actuate a function of said handheld surgical instrument connected to said associated instrument port;

said controller further configured to activate a footswitch visual indicator and an instrument visual indicator of said associated instrument port to display outputs that correspond with one another.

XXXV. A console-based surgical system comprising:

a plurality of handheld surgical instruments, each instrument having an instrument visual indicator coupled to said instrument;

a footswitch having a footswitch visual indicator coupled to said footswitch; and a console comprising:

a plurality of instrument ports, said connector lines of said plurality of handheld instruments being connected to said plurality of instrument ports;

a footswitch port; and a controller configured to associate said footswitch port with one of said instrument ports such that said footswitch is operable to actuate a function of said handheld surgical instrument connected to said associated instrument port;

said controller further configured to activate said footswitch visual indicator and said instrument visual indicator of said associated instrument port to display outputs that correspond with one another.

What is claimed is:

1. A console-based surgical system comprising:

a footswitch having a footswitch connector line and an input visual indicator comprising a light emitter;

a surgical console comprising:
- a plurality of instrument ports, each of said instrument ports having an instrument visual indicator and being configured to couple to a handheld surgical instrument and transmit an energization signal to the handheld surgical instrument;
- a footswitch port having a footswitch visual indicator and being configured to couple to said footswitch via said footswitch connector line and receive a signal from said footswitch;
- wherein each of said footswitch visual indicator and said instrument visual indicators comprises a light emitter and a ring-shaped light guide coupled to said surgical console and surrounding a corresponding one of said footswitch port and said plurality of instrument ports; and
- a controller configured to:
  - associate said footswitch port with an instrument port of said plurality of instrument ports;
  - activate said light emitter of each of said input visual indicator, said footswitch visual indicator, and said instrument visual indicator of said instrument port to emit a colored light that matches one another in response to associating said footswitch port with said instrument port;
  - receive a signal from said footswitch via said footswitch port; and
  - generate an energization signal for transmission to a handheld surgical instrument coupled to said instrument port in response to receiving the signal from said footswitch and in response to associating said footswitch port with said instrument port such that said footswitch is operable to actuate a function of the handheld surgical instrument connected to said instrument port.

2. The console-based surgical system of claim 1, wherein said footswitch comprises a base and a pedal movably coupled to said base, said base comprising said input visual indicator.

3. The console-based surgical system of claim 2, wherein said input visual indicator is positioned to illuminate an underside of said pedal.

4. The console-based surgical system of claim 1, wherein said input visual indicator is coupled to said footswitch connector line.

5. The console-based surgical system of claim 4, wherein said input visual indicator is further defined as a first input visual indicator, wherein said footswitch has a second input visual indicator comprising a light emitter, and wherein said controller is configured to activate said light emitter of said second input visual indicator to emit a colored light to match the colored light emitted by said light emitter of each of said first input visual indicator, said footswitch visual indicator, and said instrument visual indicator.

6. The console-based surgical system of claim 1, wherein said light emitter of said input visual indicator is further defined as a first footswitch light emitter, wherein said input visual indicator further comprises a second footswitch light emitter, and wherein said first footswitch light emitter is configured to output a colored light of a first color, and said second footswitch light emitter is configured to output a colored light of a second color, with said first color being different from said second color.

7. The console-based surgical system of claim 1, wherein said instrument visual indicator of said instrument port is further defined as a first instrument visual indicator, wherein said console-based surgical system further comprises a handheld surgical instrument having an instrument connector line, wherein said instrument port is connected to said handheld surgical instrument via said instrument connector line, said handheld surgical instrument having a second instrument visual indicator comprising a light emitter, and wherein said controller is configured to activate said light emitter of said second instrument visual indicator to emit a colored light to match the colored light emitted by said light emitter of each of said input visual indicator, said footswitch visual indicator, and said first instrument visual indicator.

8. The console-based surgical system of claim 7, wherein said second instrument visual indicator is coupled to said instrument connector line.

9. The console-based surgical system of claim 8, wherein said handheld surgical instrument has a third instrument visual indicator comprising a light emitter, and wherein said controller is configured to activate said light emitter of said third instrument visual indicator to emit a colored light to match the colored light emitted by said light emitter of each of said input visual indicator, said footswitch visual indicator, said first instrument visual indicator, and said second instrument visual indicator.

10. The console-based surgical system of claim 1, wherein said footswitch is further defined as a first footswitch, said input visual indicator is further defined as a first input visual indicator, said footswitch connector line is further defined as a first footswitch connector line, said footswitch port is further defined as a first footswitch port, and said footswitch visual indicator is further defined as a first footswitch visual indicator, and further comprising:
- a second footswitch having a second footswitch connector line and a second input visual indicator comprising a light emitter; and
- a second footswitch port having a second footswitch visual indicator and being configured to couple to said second footswitch via said second footswitch connector line and receive a signal from said second footswitch, wherein said second footswitch visual indicator comprises a light emitter and a ring-shaped light guide coupled to said surgical console and surrounding said second footswitch visual indicator.

11. The console-based surgical system of claim 10, wherein said controller is further configured to:
- associate said second footswitch port with said instrument port;
- activate said light emitter of each of said second input visual indicator, said second footswitch visual indicator, and said instrument visual indicator of said instrument port to emit a colored light that matches one another in response to associating said second footswitch port with said instrument port;
- receive a signal from said second footswitch via said second footswitch port; and
- generate an energization signal for transmission to a handheld surgical instrument coupled to said instrument port in response to receiving the signal from the second footswitch and in response to associating said second footswitch port with said instrument port such that said second footswitch is operable to actuate a function of the handheld surgical instrument connected to said instrument port.

12. The console-based surgical system of claim 10, wherein said instrument port is further defined as a first instrument port and said instrument visual indicator of said first instrument port is further defined as a first instrument visual indicator, and wherein said controller is further configured to:

associate said second footswitch port with a second instrument port of said plurality of instrument ports, said second instrument port having a second instrument visual indicator;

activate said light emitter of each of said second input visual indicator, said second footswitch visual indicator, and said second instrument visual indicator to emit a colored light that matches one another when said controller associates said second footswitch port with said second instrument port;

receive a signal from said second footswitch via said second footswitch port; and generate an energization signal for transmission to a handheld surgical instrument coupled to said second instrument port in response to receiving the signal from the second footswitch and in response to associating said second footswitch port with said second instrument port such that said second footswitch is operable to actuate a function of the handheld surgical instrument connected to said second instrument port.

13. The console-based surgical system of claim 10, wherein said first footswitch visual indicator and said instrument visual indicators each comprise one or more light emitters, wherein said ring-shaped light guide of said first footswitch visual indicator and said instrument visual indicators each comprises a first light emitter portion and a second light emitter portion, and wherein a light emitter is disposed within each of said first light emitter portions and each of said second light emitter portions, said light emitters being configured to emit a colored light.

14. The console-based surgical system of claim 13, wherein said light emitter disposed within said first light emitter portion of said instrument visual indicator is configured to emit a colored light of a first color and said light emitter disposed within said second light emitter portion of said instrument visual indicator is configured to emit a colored light of a second color, with the first color being different from the second color.

15. The console-based surgical system of claim 13, wherein said controller is further configured to:

associate both of said first footswitch port and said second footswitch port with said instrument port;

activate said light emitter of said first input visual indicator, said first footswitch visual indicator, and said light emitter disposed within said first light emitter portion of said instrument visual indicator to emit a colored light that matches one another in response to associating said first footswitch port with said instrument port;

activate said light emitter of each of said second input visual indicator, said second footswitch visual indicator, and said light emitter disposed within said second light emitter portion of said instrument visual indicator to emit a colored light that matches one another in response to associating said second footswitch port with said instrument port;

receive a signal from said first footswitch via said first footswitch port;

receive a signal from said second footswitch via said second footswitch port;

generate an energization signal for transmission to a handheld surgical instrument coupled to said instrument port in response to receiving the signal from the first footswitch and in response to associating said first footswitch port with said instrument port such that said first footswitch is operable to actuate a function of the handheld surgical instrument connected to said instrument port; and generate an energization signal for transmission to the handheld surgical instrument coupled to said instrument port in response to receiving the signal from the second footswitch and in response to associating said second footswitch port with said instrument port such that said second footswitch is operable to actuate a function of the handheld surgical instrument connected to said instrument port.

16. The console-based surgical system of claim 1, wherein at least one of said ring-shaped light guides coupled to said surgical console comprises a first arcuate light emitter portion and a second arcuate light emitter portion on opposing sides of said corresponding port, a first light emitter being disposed within said first arcuate light emitter portion and a second light emitter being disposed within said second arcuate light emitter portion, said first light emitter being configured to emit a colored light of a first color and said second light emitter being configured to emit a colored light of a second color.

17. The console-based surgical system of claim 16, wherein at least one of said first arcuate light emitter portion and said second arcuate light emitter portion angularly extends approximately 180 degrees.

18. The console-based surgical system of claim 1, further comprising a touchscreen panel having a plurality of icons contactable by a user, wherein contact of an icon by the user outputs a user output signal, and wherein said controller is further configured to associate said footswitch port to an instrument port of the plurality of instrument ports based on the user output signal.

19. The console-based surgical system of claim 1, wherein the colored light emitted by said light emitter of each of said input visual indicator, said footswitch visual indicator, and said instrument visual indicator of said instrument port is of a first color, and wherein said controller is configured to activate said light emitter of an instrument visual indicator of an instrument port of said plurality of instrument ports that is not associated with said footswitch port to emit a colored light of a second color, with said first color being different from said second color, to indicate that said unassociated instrument port is not associated with said footswitch port.

* * * * *